United States Patent
Yang et al.

(10) Patent No.: US 11,986,561 B2
(45) Date of Patent: *May 21, 2024

(54) WOUND DRESSINGS AND APPLICATIONS THEREOF

(71) Applicants: THE PENN STATE RESEARCH FOUNDATION, University Park, PA (US); BOARD OF REGENTS, THE UNIVERSITY OF TEXAS SYSTEM, Austin, TX (US)

(72) Inventors: Jian Yang, State College, PA (US); Kytai T. Nguyen, Grand Prairie, TX (US); Zhiwei Xie, State College, PA (US)

(73) Assignees: THE PENN STATE RESEARCH FOUNDATION, University Park, PA (US); BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 164 days.

This patent is subject to a terminal disclaimer.

(21) Appl. No.: 17/499,221

(22) Filed: Oct. 12, 2021

(65) Prior Publication Data
US 2022/0023484 A1    Jan. 27, 2022

Related U.S. Application Data

(63) Continuation of application No. 14/891,862, filed as application No. PCT/US2014/038942 on May 21, 2014, now Pat. No. 11,173,227.
(Continued)

(51) Int. Cl.
*A61L 15/22* (2006.01)
*A61L 15/26* (2006.01)
(Continued)

(52) U.S. Cl.
CPC .............. *A61L 15/225* (2013.01); *A61L 15/26* (2013.01); *A61L 15/28* (2013.01); *A61L 15/425* (2013.01);
(Continued)

(58) Field of Classification Search
CPC ...... A61L 31/129; A61L 15/28; A61L 31/042; A61L 15/26; A61L 31/06; A61L 31/16;
(Continued)

(56) References Cited

U.S. PATENT DOCUMENTS 6,319,264 B1   11/2001   Tormala et al.
8,530,611 B2   9/2013    Yang et al.
(Continued)

FOREIGN PATENT DOCUMENTS

CN   101804218   8/2010
CN   102657898   9/2012
(Continued)

OTHER PUBLICATIONS

Office Action issued by the Canadian Intellectual Property Office in Application No. 2,912,782 dated Apr. 16. 5 pages.
(Continued)

*Primary Examiner* — Michael B. Pallay
(74) *Attorney, Agent, or Firm* — Meunier Carlin & Curfman LLC

(57) ABSTRACT

In one aspect, compositions and wound dressings are described herein. In some embodiments, a composition or wound dressing described herein comprises a mesh formed from a plurality of biodegradable polymer fibers; a first active agent dispersed in the biodegradable polymer fibers; a plurality of biodegradable polymer particles disposed in the mesh; and a second active agent dispersed in the biodegradable polymer particles. The particles can be disposed within the interiors of the fibers of the mesh or between the
(Continued)

fibers of the mesh. In another aspect, a composition or wound dressing described herein comprises a first perforated mesh formed from a first plurality of biodegradable polymer fibers; and a second perforated mesh formed from a second plurality of biodegradable polymer fibers, wherein the second perforated mesh is disposed on the first perforated mesh in a stacked configuration and the first and second perforated meshes have different degrees of perforation.

15 Claims, 20 Drawing Sheets

Related U.S. Application Data

(60) Provisional application No. 61/826,328, filed on May 22, 2013.

(51) Int. Cl.

| *A61L 15/28* | (2006.01) |
|---|---|
| *A61L 15/42* | (2006.01) |
| *A61L 15/44* | (2006.01) |
| *A61L 15/64* | (2006.01) |
| *A61L 31/04* | (2006.01) |
| *A61L 31/06* | (2006.01) |
| *A61L 31/12* | (2006.01) |
| *A61L 31/14* | (2006.01) |
| *A61L 31/16* | (2006.01) |
| *C08L 67/04* | (2006.01) |

(52) U.S. Cl.
CPC .............. *A61L 15/44* (2013.01); *A61L 15/64* (2013.01); *A61L 31/042* (2013.01); *A61L 31/06* (2013.01); *A61L 31/129* (2013.01); *A61L 31/146* (2013.01); *A61L 31/148* (2013.01); *A61L 31/16* (2013.01); *C08L 67/04* (2013.01); *A61L 2300/252* (2013.01); *A61L 2300/404* (2013.01); *A61L 2300/414* (2013.01); *A61L 2300/45* (2013.01); *A61L 2300/604* (2013.01); *A61L 2300/624* (2013.01)

(58) Field of Classification Search
CPC ...... A61L 15/225; A61L 15/425; A61L 15/44; A61L 15/64; A61L 2300/252; A61L 2300/404; A61L 2300/414; A61L 2300/45; A61L 2300/604; A61L 2300/624; A61L 31/146; A61L 31/148; C08L 1/26; C08L 5/08; C08L 71/02; C08L 67/04
See application file for complete search history.

(56) References Cited

U.S. PATENT DOCUMENTS

| 8,574,311 | B2 | 11/2013 | Yang et al. |
|---|---|---|---|
| 8,613,944 | B2 | 12/2013 | Yang et al. |
| 11,173,227 | B2* | 11/2021 | Yang ..................... A61L 15/225 |
| 2005/0158362 | A1 | 7/2005 | Wheatley |
| 2008/0038354 | A1 | 2/2008 | Slager |
| 2010/0166854 | A1 | 7/2010 | Michniak-Kohn |
| 2011/0052663 | A1 | 3/2011 | Roberts |
| 2011/0124765 | A1 | 5/2011 | Yang |
| 2014/0035177 | A1 | 2/2014 | Lipton |
| 2014/0112973 | A1 | 4/2014 | Steinberg |
| 2015/0250927 | A1* | 9/2015 | MacEwan ................ B32B 7/02 |
| | | | 606/151 |

FOREIGN PATENT DOCUMENTS

| EP | 2508212 | 10/2012 |
|---|---|---|
| JP | 10-511019 | 10/1998 |
| JP | 2005522594 A | 7/2005 |
| JP | 2011-200653 | 10/2011 |
| WO | 9951163 | 10/1999 |
| WO | 2006/116000 | 11/2006 |
| WO | 2012/099703 | 7/2012 |
| WO | 2012/175611 | 12/2012 |

OTHER PUBLICATIONS

Notification of Reexamination issued by the State Intellectual Property Office of the People's Republic of China in Application No. 2014800414626 dated May 13, 2020. 16 pages.
Liu, Zhongchu, Chemical Industry Press, Aug. 2006, the first edition, p. 138, publication date: Aug. 31, 2006 (Non-official translation: Comprehensive Utilization of Marine Biological Resources).
Li, Quanlin, China Medicical Science and Technology Press, Dec. 2008, the 1st edition, p. 1104, publication date: Dec. 31, 2008 (Non-official translation: Development and Research of New Medicine).
Translation of Notice of Reasons for Refusal issued for Japanese Patent Application No. 2016-515044, dated Jan. 30, 2018.
Translation Decision to Grant, issued for Japanese Patent Application No. 2016-515044, dated Sep. 25, 2018.
Losi et al., "Fibrin-based scaffold incorporating VEGF- and bFGF-loaded nanoparticles stimulates wound healing in diabetic mice", available online Apr. 17, 2013, Acta Biomaterialia, vol. 9, issue 8, pp. 7814-7821. (Year: 2013).
Choi et al., Coaxial Electrospun Nanofibers for Treatment of Diabetic Ulcers with Binary Release of Multiple Growth Factors, Journal of Materials of Chemistry, vol. 12, pp. 5258-5267, 2011.
Ulubayram, EGF Containing-Gelatin Wound Dressing, Biomaterials, vol. 22, pp. 1345-1356, 2001.
Richardson, Polymeric System for Dual Growth Factor Delivery, Nature Biotechnology, vol. 19, pp. 1029-1034, 2001.
PCT International Search Report and Written Opinion dated Jan. 1, 2015, for PCT/US2014/038942.
Menon et al., Effects of surfactants on the properties of PLGA nanoparticles, Journal of Biomedical Materials Research, Part A, 2012, 100, 1998-2005.

* cited by examiner

FIG. 2A    FIG. 2B    FIG. 2C
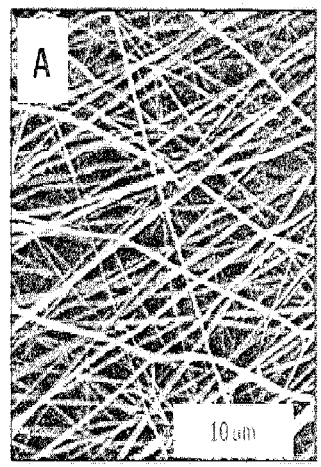
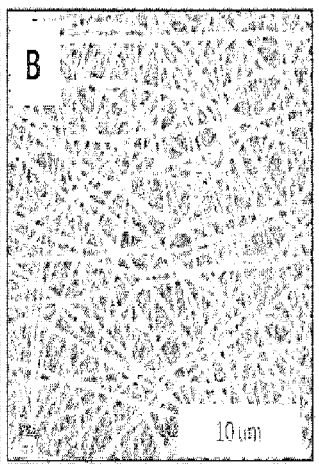
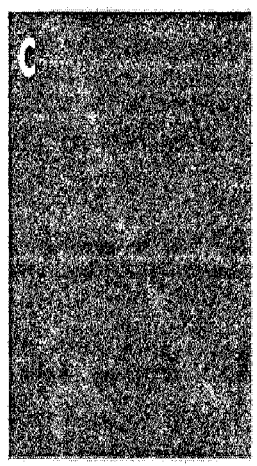
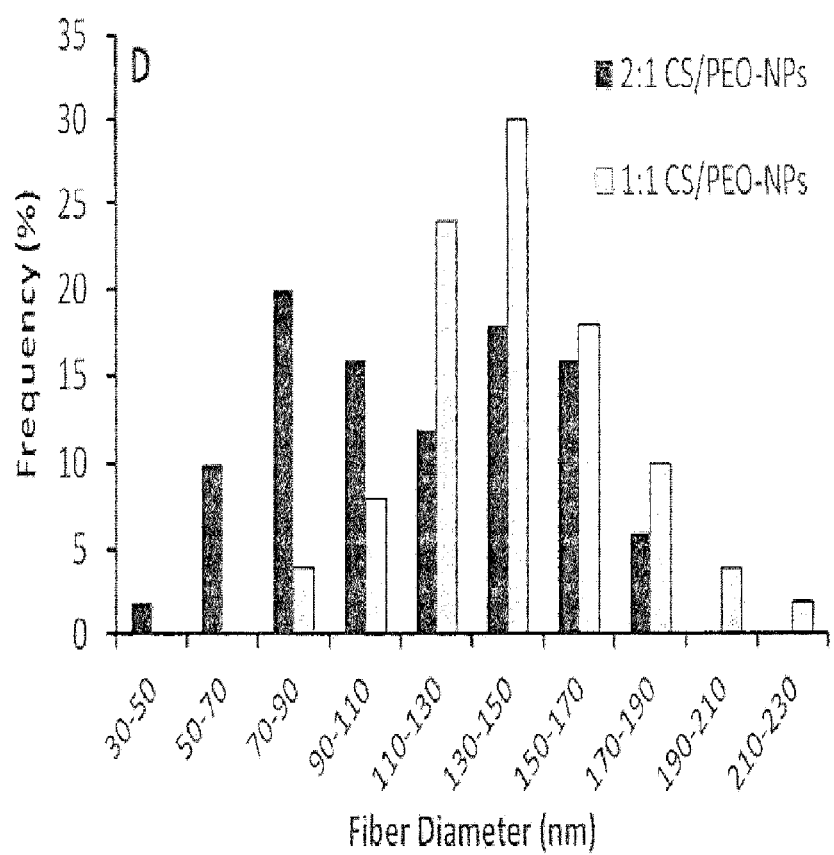
FIG. 2D

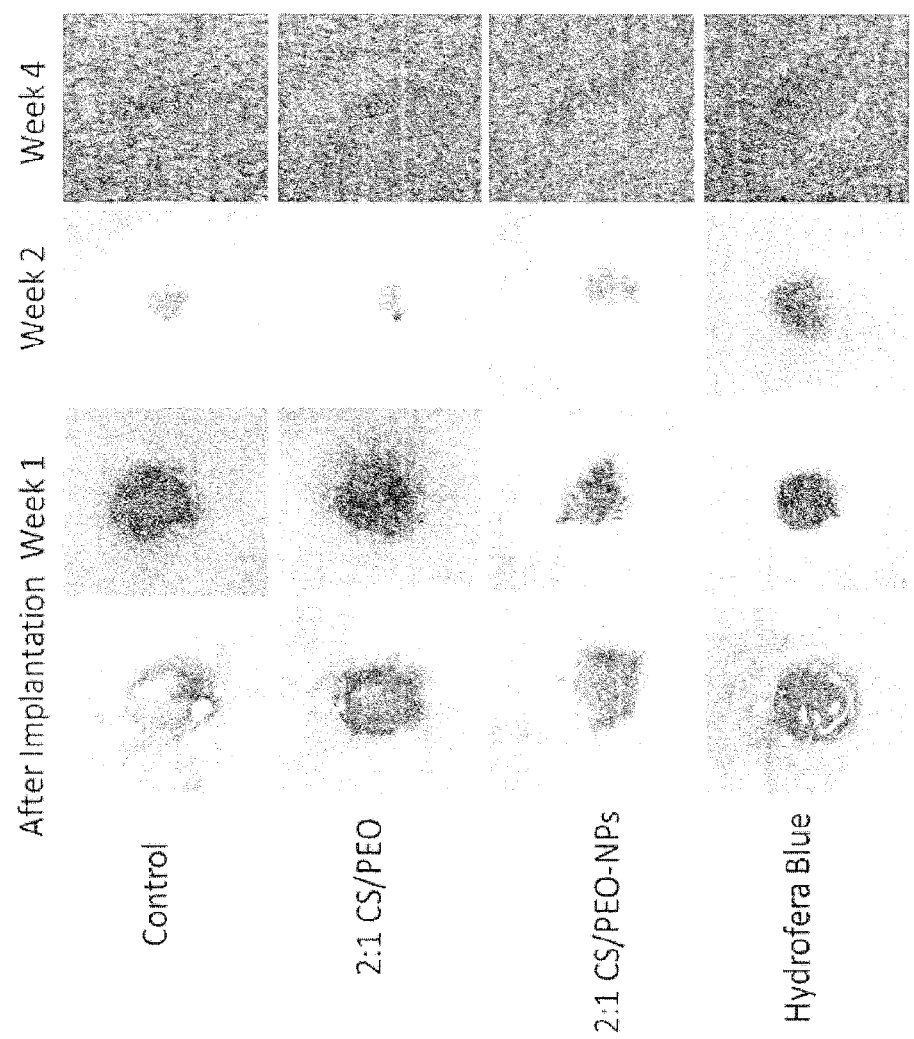

WOUND DRESSINGS AND APPLICATIONS THEREOF

CROSS REFERENCE TO RELATED APPLICATIONS

This application is a continuation application of the U.S. Non-Provisional application Ser. No. 14/891,862, filed on Nov. 17, 2015, which is a national phase entry of an International Patent Application No. PCT/US2014/038942, filed on May 21, 2014, which claims priority pursuant to 35 U.S.C. § 119 to U.S. Provisional Application No. 61/826,328, filed May 22, 2013, the contents of which are hereby incorporated by reference in their entirety.

STATEMENT REGARDING FEDERALLY SPONSORED RESEARCH

This invention was made with government support under contract EB012575 awarded by the National Institute of Biomedical Imaging and Bioengineering (NIBIB), and contract DMR1313553 awarded by the National Science Foundation (NSF). The government has certain rights in the invention.

FIELD

This invention relates to compositions and wound dressings and, in particular, to compositions and wound dressings comprising biodegradable polymer fibers and biodegradable polymer particles.

BACKGROUND

Wound healing is a dynamic and complex process involving extracellular matrix (ECM), cytokines, blood cells, and other biological species. Further, wound healing can include three overlapping phases: inflammation, tissue regeneration, and tissue remodeling. Due to the pathological and physiological complexity of the wound healing process, perfect tissue regeneration can be difficult to achieve, especially for skin wounds and chronic wounds such as diabetic ulcers and hernias. Hernia repair is one of the most common surgeries in the United States, where up to 27% of men and 3% women are affected by hernias. Unfortunately, some existing hernia repair procedures and devices, such as non-biodegradable hernia repair meshes, can themselves cause chronic pain and/or recurrence of the hernia. For example, some existing meshes exhibit poor cell infiltration into the mesh and/or poor mechanical performance.

Further, many existing wound dressings act only as temporary barriers for hemostasis to protect the patient from infection and do not otherwise promote wound healing. In addition, some natural and synthetic skin graft applications can be expensive, require extensive post-procedure care, and/or fail to provide full skin functionality. Therefore, there exists a need for improved wound dressings and methods of treating wounds such as skin wounds, diabetic ulcers, and hernias.

SUMMARY

In one aspect, compositions and wound dressings are described herein which, in some embodiments, can provide one or more advantages compared to some other compositions and wound dressings. For example, in some embodiments, a composition or wound dressing described herein can promote more rapid wound healing through the controlled release of a plurality of active agents according to a desired release profile, including a bimodal or partially overlapping release profile. A composition or wound dressing described herein can also promote wound healing by presenting a compositional gradient to a wound site, such as a porosity or perforation gradient. Moreover, in some cases, a composition or wound dressing described herein can provide a fibrous scaffold for supporting cell growth, including regenerated cell growth. Such a fibrous scaffold, in some instances, can mimic the extracellular matrix (ECM) of living organisms. In addition, a fibrous scaffold provided by a composition or wound dressing described herein can also exhibit antimicrobial properties. Moreover, compositions or wound dressings described herein can provide one or more of the foregoing advantages simultaneously. For example, in some cases, a composition or wound dressing described herein can serve as a scaffold to support wound healing while also releasing multiple active agents at various phases of wound healing. In some embodiments, a composition or wound dressing described herein can simultaneously provide biochemical stimulation, cell growth support, and bacteria inhibition.

In some embodiments, a composition described herein comprises a biodegradable polymer fiber, a first active agent dispersed within the fiber, a plurality of biodegradable polymer particles dispersed within the fiber, and a second active agent dispersed within the polymer particles. In addition, in some cases, a composition or wound dressing described herein comprises a mesh formed from a plurality of biodegradable polymer fibers; a first active agent dispersed in the biodegradable polymer fibers; a plurality of biodegradable polymer particles disposed in the mesh; and a second active agent dispersed in the biodegradable polymer particles. In some embodiments, the particles are disposed within the interiors of the fibers of the mesh. Alternatively, in other cases, the particles are disposed between the fibers of the mesh. Additionally, the mesh of a composition or wound dressing described herein can be a nonwoven mesh.

As described further hereinbelow, a composition or wound dressing having a structure described herein, in some embodiments, can provide a bifurcated, bimodal, or temporally separated delivery of the first and second active agents to a wound or other biological compartment when the wound dressing is disposed on the wound or in the biological compartment.

One or more active agents of a composition or wound dressing described herein, in some cases, can comprise a growth factor, such as a growth factor for angiogenesis, wound healing, or bone growth. Moreover, in some embodiments, the identity of one or more growth factors is selected to achieve one or more desired biological effects, including in a desired temporal sequence. In some instances, for example, a first active agent is selected to achieve a first biological effect, such as promotion of blood vessel growth, and a second active agent is selected to achieve a second biological effect, such as wound healing or the promotion of bone growth, that may desirably be temporally separated from the first biological effect.

Additionally, in some embodiments, the biodegradable polymer fibers of a composition or wound dressing described herein comprise one or more antimicrobial polymer fibers. In some cases, the biodegradable polymer fibers comprise one or more of chitosan, carboxymethyl chitosan (CMC), poly(ethylene oxide), and collagen. In other embodiments, the biodegradable polymer fibers of a composition or wound dressing described herein comprise one or more polymers comprising a citrate moiety. Moreover, in some instances, the biodegradable polymer fibers are nanofibers having an average diameter between about 50 nm and about 1000 nm. Similarly, in some cases, the biodegradable polymer particles of a composition or wound dressing described herein are nanoparticles having an average size between about 10 nm and about 200 nm.

In another aspect, compositions or wound dressings described herein comprise a stack of biodegradable polymer fiber meshes that may or may not comprise biodegradable polymer particles and/or active agents. In some embodiments, such a stack of meshes is arranged to provide a property gradient in the z-direction, as described further hereinbelow. For example, in some cases, a composition or wound dressing described herein comprises a first perforated mesh formed from a first plurality of biodegradable polymer fibers; and a second perforated mesh formed from a second plurality of biodegradable polymer fibers, wherein the second perforated mesh is disposed on the first perforated mesh in a stacked configuration and the first perforated mesh has a higher degree of perforation than the second perforated mesh. Additionally, in some embodiments, such a composition or wound dressing further comprises a third perforated mesh formed from a third plurality of biodegradable polymer fibers, wherein the third perforated mesh is disposed on the second perforated mesh in a stacked configuration and the third perforated mesh has a higher degree of perforation than the first perforated mesh and the second perforated mesh. Moreover, as described further hereinbelow, compositions or wound dressings described herein can further comprise additional perforated meshes or non-perforated meshes in a stacked configuration. For example, in some cases, a composition or wound dressing described herein further comprises a fourth mesh formed from a fourth plurality of biodegradable polymer fibers, wherein the fourth mesh is non-perforated or has a lower degree of perforation than the third perforated mesh. A wound dressing having such a structure, in some embodiments, can provide a physical barrier to complete tissue penetration of the wound dressing on the side of the wound dressing farther from the wound.

Additionally, if desired, one or more meshes of a stack described herein can have a structure described hereinabove for wound dressings comprising active agents. For example, in some cases, an active agent is dispersed in the biodegradable polymer fibers of the first perforated mesh and/or the second perforated mesh. In some instances, a plurality of biodegradable polymer particles is disposed in the first perforated mesh and/or the second perforated mesh. Moreover, in some cases, a second active agent is dispersed in the biodegradable polymer particles.

In another aspect, methods of treating a wound are described herein. In some embodiments, a method of treating a wound described herein comprises applying a composition or wound dressing described hereinabove to a surface of the wound, which may be a skin wound, diabetic ulcer, or hernia. For example, in some embodiments, the wound dressing comprises a mesh formed from a plurality of biodegradable polymer fibers; a first active agent dispersed in the biodegradable polymer fibers; a plurality of biodegradable polymer particles disposed in the mesh; and a second active agent dispersed in the biodegradable polymer particles. Such a method, in some cases, can further comprise at least partially degrading the biodegradable polymer fibers to release one or more active agents into the wound.

These and other embodiments are described in more detail in the detailed description which follows.

BRIEF DESCRIPTION OF THE FIGURES

FIGS. 2A and 2B illustrate scanning electron microscope (SEM) images of meshes of wound dressings according to some embodiments described herein.

FIG. 2C illustrates a fluorescence image of a wound dressing according to one embodiment described herein.

FIG. 2D illustrates plots of the diameters of polymer fibers of wound dressings according to some embodiments described herein.

FIG. 6A illustrates photographs of wounds treated according to some embodiments of methods described herein.

DETAILED DESCRIPTION

Figure 1:
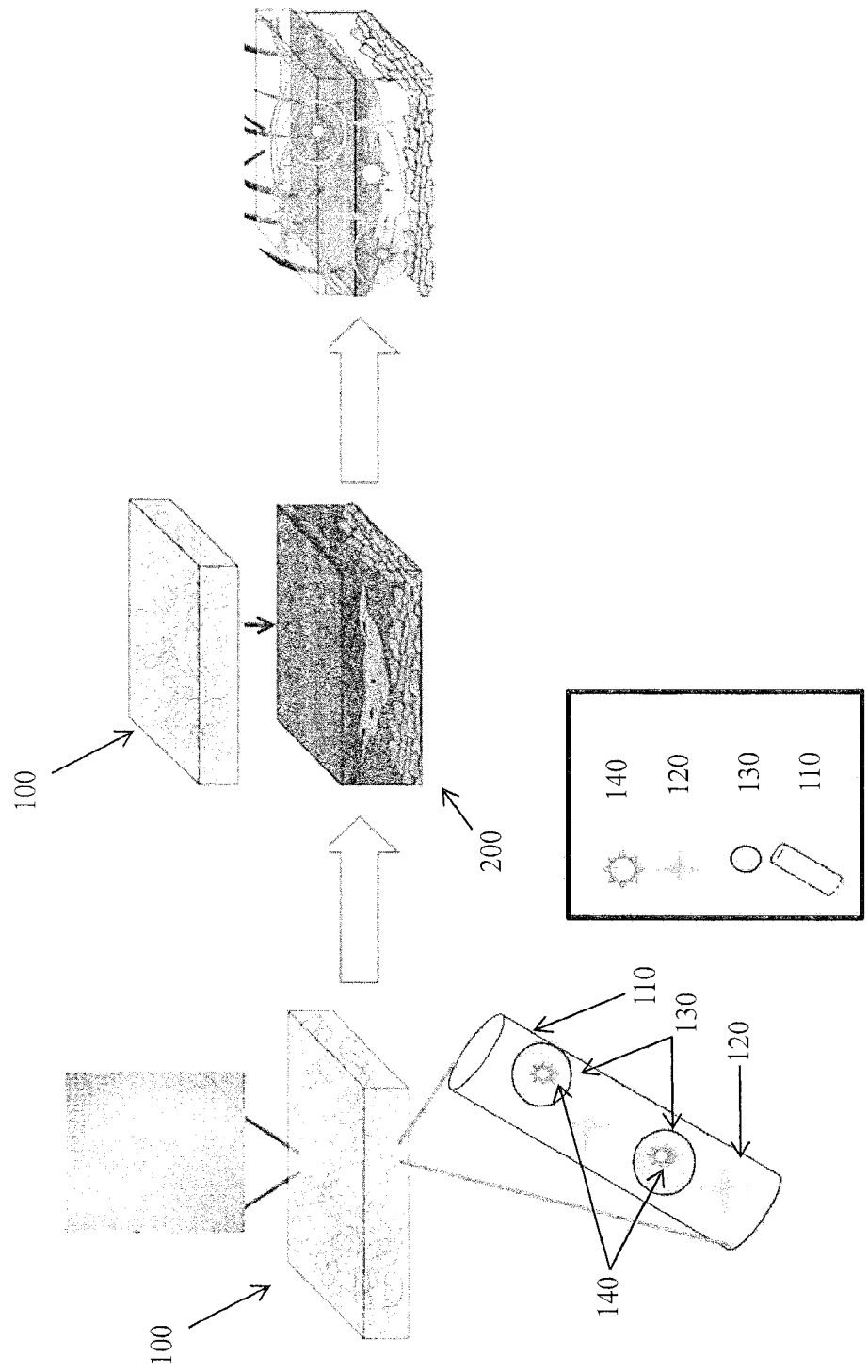
FIG. 1 illustrates schematically a wound dressing and a method of treating a wound according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Compositions and Wound Dressings

In one aspect, compositions and wound dressings are described herein. In some embodiments, a composition described herein comprises a biodegradable polymer fiber, a first active agent dispersed within the fiber, a plurality of biodegradable polymer particles dispersed within the fiber, and a second active agent dispersed within the polymer particles. In addition, in some cases, a composition or wound dressing described herein comprises a mesh formed from a plurality of biodegradable polymer fibers; a first active agent dispersed in the biodegradable polymer fibers; a plurality of biodegradable polymer particles disposed in the mesh; and a second active agent dispersed in the biodegradable polymer particles. In some cases, the particles are disposed within the fibers of the mesh, such that the fibers completely or substantially completely contain the particles within the interior volumes of the fibers. In such instances, the polymer particles can be present within the polymer fibers in any amount not inconsistent with the objectives of the present disclosure. In some embodiments, for example, the biodegradable polymer particles are present within the fibers in an amount up to about 30 weight percent, based on the total weight of the fibers plus the particles. In other cases, the biodegradable polymer particles are present within the fibers in an amount up to about 25 weight percent, up to about 20 weight percent, up to about 15 weight percent, up to about 10 weight percent, or up to about 5 weight percent, based on the total weight of the fibers plus the particles. In some embodiments, the biodegradable polymer particles are present within the fibers in an amount between about 1 weight percent and about 30 weight percent, between about 5 weight percent and about 25 weight percent, between about 5 weight percent and about 20 weight percent, between about 5 weight percent and about 15 weight percent, or between about 10 weight percent and about 20 weight percent, based on the total weight of the fibers plus the particles. Fibers comprising such amounts of particles, in some embodiments, can be smooth, uniform, and substantially beadless composite fibers.

In some cases, the biodegradable polymer particles of a wound dressing described herein are disposed between the fibers of the mesh. Particles that are disposed between the fibers of the mesh can be physically entrapped in the mesh and/or chemically bonded to the outer surface of the fibers of the mesh, as opposed to being incorporated into the interior volume of the fibers. In such cases, the biodegradable polymer particles can be present in the mesh in any amount not inconsistent with the objectives of the present disclosure. In some embodiments, the biodegradable polymer particles can be present in the mesh in an amount up to about 80 weight percent, up to about 70 weight percent, up to about 50 weight percent, up to about 40 weight percent, up to about 30 weight percent, up to about 20 weight percent, up to about 10 weight percent, or up to about 5 weight percent, based on the total weight of the mesh plus the particles. In some cases, the biodegradable polymer particles are present in the mesh in an amount between about 1 weight percent and about 80 weight percent, between about 5 weight percent and about 70 weight percent, between about 10 weight percent and about 50 weight percent, between about 10 weight percent and about 40 weight percent, or between about 10 weight percent and about 20 weight percent, based on the total weight of the mesh plus the particles.

As described further hereinbelow, a wound dressing having a structure described herein, in some embodiments, can provide a bifurcated, bimodal, or temporally separated delivery of the first and second active agents to a wound or other biological compartment when the wound dressing is disposed in contact with the wound or other biological compartment. In some cases, such a release profile can be achieved even when the first and second active agents are chemically similar and/or when the biodegradable polymer fibers are chemically similar to the biodegradable polymer particles. For example, first and second active agents having the same or similar hydrophobicity, hydrophilicity, electrostatic charge, and/or hydrodynamic size can nevertheless exhibit different in vivo or in vitro release profiles when included in a wound dressing having a structure described herein. An "in vivo or in vitro release profile," for reference purposes herein, describes the amount or concentration of an active agent that is released from a wound dressing over time (t) when the wound dressing is disposed in an in vivo or in vitro environment, respectively. Such release of an active agent may occur due to diffusion of the active agent out of the biodegradable polymer fibers or particles in which the active agent is dispersed. Release of an active agent may also occur due to degradation of the biodegradable polymer fibers or particles.

In some embodiments, the in vivo or in vitro release profile of the first active agent of a wound dressing described herein differs from the in vivo or in vitro release profile of the second active agent. For example, in some cases, the in vivo or in vitro release profile of the first active agent and the in vivo or in vitro release profile of the second active agent overlap by less than about 70%. In some embodiments, the release profiles overlap by less than about 50%, less than about 40%, less than about 30%, less than about 25%, less than about 20%, less than about 15%, less than about 10%, less than about 5%, or less than about 1%. In some instances, the release profiles are entirely non-overlapping.

The percent "overlap" of active agent release profiles can be based on the total area of the in vivo or in vitro release profile curves of the active agents, as described further hereinbelow. For example, a first active agent may be completely released from a wound dressing described herein beginning at 3 days after placement of the wound dressing and ending at 7 days after placement. A second active agent may begin to be released from the wound dressing after 7 days after placement. In such an instance, the in vivo or in vitro release profile of the first active agent would overlap the in vivo or in vitro release profile of the second active agent by 0%. Alternatively, if half of the total amount of the first active agent were released between t=6 days and t=7 days (with the other half being released prior to t=6 days), and half of the total amount of the second active agent were released between t=6 days and t=7 days (with the other half being released after t=7 days), then the in vivo or in vitro release profiles of the first and second active agents would overlap by 50%.

In general, a desired overlap between the in vivo or in vitro release profiles of active agents described herein can be selected based on one or more of the following: the chemical composition of each of the active agents, the chemical composition of the biodegradable polymer fibers, the chemical composition of the biodegradable polymer particles, the amount of active agent dispersed in each of the biodegradable polymer fibers and particles, the physical dimensions of the biodegradable polymer fibers and particles, and the biodegradation rates of the biodegradable polymer fibers and particles. Further, in some cases, each of the foregoing features can be used independently to increase or decrease the overlap of active agent release profiles. For example, to achieve a higher percent overlap, the chemical composition of the first and second active agents can be selected to exhibit the same or similar hydrophobicity, hydrophilicity, electrostatic charge, and/or hydrodynamic size. A higher percent overlap can also be achieved by providing biodegradable polymer fibers and biodegradable polymer particles having similar chemical compositions, similar biodegradation rates, and/or similar sizes. In contrast, to achieve a lower percent overlap of in vivo or in vitro release profiles, the foregoing properties of the first and second active agents can differ. It is also possible to achieve a lower percent overlap of in vivo or in vitro release profiles by dispersing a hydrophobic first active agent in hydrophilic biodegradable polymer fibers and dispersing a hydrophilic second active agent in hydrophilic biodegradable polymer particles. A desired overlap of release profiles can be achieved in other ways as well.

Similarly, the absolute release rates of the first and second active agents can also be independently selected based on one or more of the foregoing factors, including one or more of the chemical composition of each of the active agents, the chemical composition of the biodegradable polymer fibers, the chemical composition of the biodegradable polymer particles, the amount of active agent dispersed in each of the biodegradable polymer fibers and particles, the physical dimensions of the biodegradable polymer fibers and particles, and the biodegradation rates of the biodegradable polymer fibers and particles. In some cases, the first active agent of a wound dressing described herein has a release half-life of less than about 4 days, less than about 3 days, less than about 2 days, or less than about 1 day. In some instances, the first active agent of a wound dressing described herein has a release half-life between about 0.5 days and about 5 days, between about 0.5 days and about 4 days, between about 1 day and about 4 days, or between about 1 day and about 3 days. In some embodiments, the first active agent has a release half-life of less than 1 day. Additionally, in some cases, the second active agent has a release half-life longer than the release half-life of the first active agent. For example, in some embodiments, the second active agent of a wound dressing described herein has a release half-life of greater than about 2 days, greater than about 3 days, greater than about 4 days, greater than about 5 days, greater than about 6 days, greater than about 7 days, or greater than about 10 days. In some instances, the second active agent has a release half-life between about 1 day and about 10 days, between about 2 days and about 9 days, between about 3 days and about 8 days, between about 3 days and about 7 days, between about 4 days and about 10 days, between about 4 days and about 7 days, or between about 4 days and about 6 days. Thus, in some embodiments, a wound dressing described herein can provide a rapid release of a first active agent (such as when the release half-life of the first active agent is less than about 2 days or less than about 1 day), followed by a slower, sustained release of a second active agent (such as when the release half-life of the second active agent is greater than about 5 days). Moreover, in some cases, such release rates can be obtained even when the first and second active agents have the same or similar hydrophobicity, hydrophilicity, hydrodynamic size, and/or electrostatic charge, including relative to the biodegradable polymer fibers and particles in which the active agents are dispersed. The "release half-life" of an active agent, for reference purposes herein, refers to the amount of time needed for half the total amount of the active agent to be released from the wound dressing following placement of the wound dressing in an in vivo or in vitro environment.

Further, in some embodiments, the first active agent of a wound dressing described herein has a release profile wherein at least about 30%, at least about 50%, or at least about 60% by weight of the active agent is released within 30 minutes of disposing the wound dressing in an in vivo or in vitro environment. In some cases, the first active agent has a release profile wherein between about 30% and about 70% or between about 30% and about 65% of the active agent is released within 30 minutes of disposing the wound dressing in an in vivo or in vitro environment. In some embodiments, the first active agent has a release profile wherein at least about 90%, at least about 95%, or at least about 99.9% by weight of the active agent is released within 3 days of disposing the wound dressing in an in vivo or in vitro environment.

Similarly, in some cases, the second active agent of a wound dressing described herein has a release profile wherein less than about 30%, less than about 20%, or less than about 15% by weight of the active agent is released during the first 24 hours after disposing the wound dressing in an in vivo or in vitro environment. In some cases the second active agent has a release profile wherein between about 1% and about 30% or between about 5% and about 25% of the active agent is released during the first 24 hours after disposing the wound dressing in an in vivo or in vitro environment. Additionally, in some embodiments, the second active agent has a sustained release profile in vivo or in vitro.

Further, although wound dressings having two active agents are described herein, it is to be understood that wound dressings can also comprise more than two active agents. For example, in some embodiments, a plurality of differing first active agents is disposed in the polymer fibers of a wound dressing, and/or a plurality of differing second active agents is disposed in the polymer particles of a wound dressing described herein.

Turning now to specific components of some wound dressings, wound dressings described herein, in some embodiments, comprise a mesh formed from biodegradable polymer fibers. Any biodegradable polymer fibers not inconsistent with the objectives of the present disclosure may be used. A biodegradable polymer, in some embodiments, degrades in vivo to non-toxic components which can be cleared from the body by ordinary biological processes. In some embodiments, a biodegradable polymer completely or substantially completely degrades in vivo over the course of about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in equation (1):

$$\text{Mass loss (\%)} = \frac{(W_0 - W_t)}{W_0} \times 100. \quad (1)$$

In some embodiments, the biodegradable polymer fibers of a mesh described herein comprise one or more antimicrobial polymer fibers, such as one or more chitosan fibers. In other cases, the biodegradable polymer fibers can include an antimicrobial material dispersed within or bonded to the surface of the fibers. Additionally, in some embodiments, biodegradable polymer fibers described herein include antimicrobial peptides encapsulated within or bonded to the surface of the fibers.

In some cases, the biodegradable polymer fibers of a wound dressing described herein comprise or are formed from one or more of chitosan, carboxymethyl chitosan (CMC), and polyethylene oxide (PEO) or polyethylene glycol (PEG). In other instances, the biodegradable polymer fibers of a wound dressing comprise or are formed from an alginate, agarose, starch, polysaccharide, cellulose or cellulose derivative, dextrin, dextran, fibrin, fibrinogen, fibronectin, collagen, gelatin, elastin, laminin, glycosaminoglycan, hyalauronic acid, albumin, polypeptide, polylactic acid (PLA), polyglycolic acid (PGA), polylactic-co-glycolic acid (PLGA), polycaprolactone (PCL), polyglycolide, polyanhydride, polyphosphazene, or polyurethane. A mixture, combination, or copolymer of one or more of the foregoing may also be used. For example, in some embodiments, a biodegradable polymer fiber described herein can include a blend of chitosan and PEO. In some instances, a fiber described herein can be formed from a blend of chitosan and PEO having a chitosan to PEO ratio between about 1:3 and about 10:1 by weight or between about 1:1 and about 5:1 by weight. Other combinations or blends of polymers described herein may also be used to form the biodegradable polymer fibers of a mesh described herein.

Moreover, in some embodiments, the biodegradable polymer fibers of a mesh described herein comprise or are formed from one or more polymers comprising a citrate moiety. A "citrate moiety," for reference purposes herein, comprises a moiety having the structure of Formula (I):

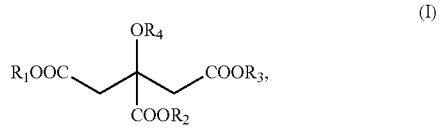

(I)

wherein $R_1$, $R_2$, and $R_3$ are independently —H, —CH$_3$, —CH$_2$CH$_3$, M$^+$, or a point of attachment to the remainder of the polymer;
$R_4$ is —H or a point of attachment to the remainder of the polymer; and
M$^+$ is a cation such as Na$^+$ or K$^+$, provided that at least one of $R_1$, $R_2$, $R_3$, and $R_4$ is a point of attachment to the remainder of the polymer.

For example, in some cases, a polymer of a composition or wound dressing described herein comprises the reaction product of (i) citric acid, a citrate, or an ester of citric acid such as triethyl citrate with (ii) a polyol such as a diol. Non-limiting examples of polyols suitable for use in some embodiments described herein include C2-C20 α,ω-n-alkane diols or C2-C20 α,ω-alkene diols. In other instances, a polymer of a wound dressing described herein comprises the reaction product of (i) citric acid, a citrate, or an ester of citric acid with (ii) a polyol, and (iii) an amine, an amide, or an isocyanate. An amine, in some cases, comprises one or more primary amines having two to ten carbon atoms. In other cases, an amine comprises one or more secondary or tertiary amines having two to fifteen carbon atoms. An isocyanate, in some embodiments, comprises a monoisocyanate. In other instances, an isocyanate comprises a diisocyanate such as an alkane diisocyanate. In addition, a polymer of a wound dressing described herein can also comprise the reaction product of (i) citric acid, a citrate, or an ester of citric acid with (ii) a polyol, and (iii) a polycarboxylic acid such as a dicarboxylic acid or a functional equivalent of a polycarboxylic acid, such as a cyclic anhydride or an acid chloride of a polycarboxylic acid. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. In still other embodiments, a polymer described herein comprises the reaction product of (i) citric acid, a citrate, or an ester of citric acid with (ii) a polyol, and (iii) an amino acid such as an alpha-amino acid. An alpha-amino acid, in some embodiments, comprises an L-amino acid, a D-amino acid, or a D,L-amino acid. In some cases, an alpha-amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 "standard" or proteinogenic amino acids, such as methyl serine. Additionally, in some cases, an amino acid forms a pendant group or side group of the polymer or oligomer of a composition described herein. Moreover, a reaction product of monomers described herein, in some cases, is a condensation reaction product of the monomers. In some cases, a polymer described herein is a polymer or oligomer described in U.S. Pat. Nos. 8,530,611; 8,574,311; or U.S. Pat. No. 8,613,944.

In addition, in some embodiments, a polymer of a wound dressing described herein is formed from one or more monomers of Formula (A) and one or more monomers of Formula (B) or (B'):

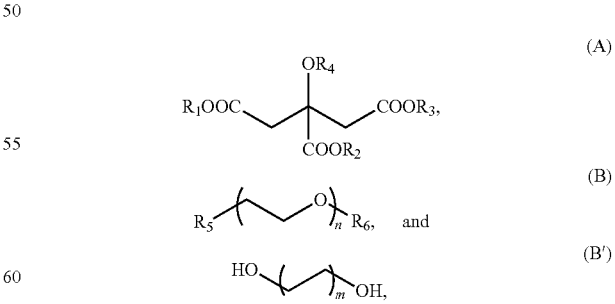

wherein $R_1$, $R_2$, and $R_3$ are independently —H, —CH$_3$, —CH$_2$CH$_3$, or M$^+$;
$R_4$ is —H;
$R_5$ is —H, —OH, —OCH$_3$, —OCH$_2$CH$_3$, —CH$_3$, or —CH$_2$CH$_3$;

$R_6$ is —H, —$CH_3$, or —$CH_2CH_3$;

$M^+$ is a cation such as $Na^+$ or $K^+$; and n and m are independently integers ranging from 1 to 20.

In some cases, for instance, $R_1$, $R_2$, and $R_3$ are —H, $R_5$ is —OH and $R_6$ is —H.

In some embodiments, a polymer of a wound dressing described herein is formed from one or more monomers of Formula (A), one or more monomers of Formula (B) or (B'), and one or more monomers of Formula (C):

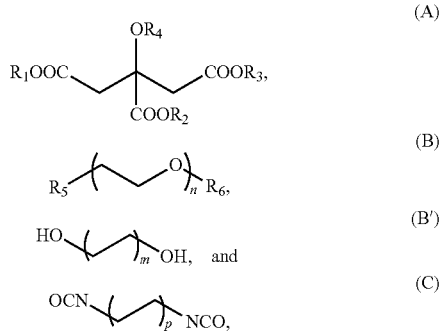

wherein $R_1$, $R_2$, and $R_3$ are independently —H, —$CH_3$, —$CH_2CH_3$, or $M^+$;

$R_4$ is —H;

$R_5$ is —H, —OH, —$OCH_3$, —$OCH_2CH_3$, —$CH_3$, or —$CH_2CH_3$;

$R_6$ is —H, —$CH_3$, or —$CH_2CH_3$;

$M^+$ is a cation such as $Na^+$ or $K^+$;

n and m are independently integers ranging from 1 to 20; and p is an integer ranging from 1 to 10.

For example, in some instances, $R_1$, $R_2$, and $R_3$ are —H, or —$CH_2CH_3$, $R_5$ is —OH, $R_6$ is n is 2 to 6, m is 2 to 8, and p is 2 to 6.

Further, in some embodiments of wound dressings described herein, a monomer of Formula (B) or (B') can be replaced by an alcohol that does not have the formula of Formula (B) or (B'). For example, in some embodiments, an unsaturated alcohol or an unsaturated polyol can be used. Moreover, in some cases, a monomer or oligomer of Formula (C) can be at least partially replaced by an amino acid described herein.

Additionally, a biodegradable polymer described herein can have at least one ester bond in the backbone of the polymer. In some cases, a polymer has a plurality of ester bonds in the backbone of the polymer, such as at least three ester bonds, at least four ester bonds, or at least five ester bonds. In some embodiments, a polymer described herein has between two ester bonds and fifty ester bonds in the backbone of the polymer.

Further, in some cases, a mesh of a wound dressing described herein can be formed from a mixture or blend of biodegradable polymer fibers formed from different polymers described herein.

Moreover, the biodegradable polymer fibers of a mesh described herein can have any size and shape not inconsistent with the objectives of the present disclosure. In some embodiments, for instance, the biodegradable polymer fibers have an average diameter of about 1000 nm or less. In some cases, polymer fibers described herein have an average diameter between about 10 nm and about 1000 nm or between about 50 nm and about 1000 nm. In some cases, polymer fibers described herein can have an average diameter between about 10 nm and about 500 nm, between about 10 nm and about 100 nm, between about 50 nm and about 500 nm, between about 100 nm and about 1000 nm, or between about 500 nm and about 1000 nm. In other instances, polymer fibers described herein have an average diameter greater than about 1000 nm. In some embodiments, polymer fibers described herein have an average diameter between about 1000 nm and about 100 μm, between about 1000 nm and about 10 μm, between about 5 μm and about 100 μm, between about 5 μm and about 50 μm, or between about 10 μm and about 100 μm.

Wound dressings described herein, in some embodiments, also comprise a first active agent dispersed in the biodegradable polymer fibers of a mesh. An "active agent," for reference purposes herein, can comprise any species operable to provide a biological effect when disposed in vivo. Any active agent not inconsistent with the objectives of the present disclosure may be used. In some embodiments, the first active agent of a wound dressing described herein comprises a growth factor. Any growth factor not inconsistent with the objectives of the present disclosure may be used. In some cases, a growth factor described herein can modulate one or more wound healing processes, such as hemostasis, cell migration, cell differentiation, ECM formation, and angiogenesis. In some embodiments, the first active agent comprises an epidermal growth factor (EGF); a heparin binding EGF; a platelet-derived growth factor (PDGF) such as PDGF-BB; a transforming growth factor beta (TGF-β) such as TGF-β-1 or TGF-β-2; a vascular endothelial growth factor (VEGF); an insulin like growth factor (IGF) such as IGF-I or IGF-II; an acidic or basic fibroblast growth factor (FGF) such as FGF-1 or FGF-2; and/or one or more isoforms of the foregoing. Other growth factors may also be used.

Moreover, in some embodiments, the identity of the first active agent of a wound dressing described herein is selected to provide a desired first biological effect, such as promotion of blood vessel growth or development. For example, in some embodiments, the first active agent comprises a growth factor for angiogenesis and/or the formation of granulation tissue, such as VEGF. In other instances, the first growth factor can comprise a PDGF, and thus may provide tissue inflammation control, granulation, re-epithelialization, and/or remodeling throughout a wound healing process.

A first active agent can be present in a mesh of a wound dressing described herein in any amount not inconsistent with the objectives of the present disclosure. For example, in some cases, a first active agent is present in the mesh in an amount up to about 20 weight percent, up to about 10 weight percent, up to about 5 weight percent, or up to about 1 weight percent, based on the total weight of the mesh.

The mesh of a wound dressing described herein can have a variety of physical and chemical characteristics. In some embodiments, for example, a mesh of a wound dressing has a high porosity. In some cases, the mesh has a porosity of up to about 90%, up to about 75%, or up to about 50%. In some embodiments, the mesh has a porosity between about 10% and about 90%, between about 10% and about 80%, between about 30% and about 90%, or between about 30% and about 70%.

A mesh of a wound dressing described herein can also have a hydrophilic surface or a hydrophobic surface. The hydrophilicity and/or hydrophobicity of a mesh described herein can be selected based on the chemical composition of one or more of the biodegradable polymer fibers used to form the mesh.

In addition, a mesh of a wound dressing described herein can have any thickness not inconsistent with the objectives of the present disclosure. In some cases, the mesh has an average thickness in the z-direction between about 10 nm and about 10 mm, between about 100 nm and about 1 mm, between about 100 nm and about 500 µm, between about 1 µm and about 10 mm, between about 1 µm and about 1 mm, between about 10 µm and about 10 mm, between about 10 µm and about 1 mm, between about 100 µm and about 10 mm, or between about 10 µm and about 1 mm. Other thicknesses are also possible.

Wound dressings described herein, in some embodiments, also comprise a plurality of biodegradable polymer particles disposed in the mesh of the wound dressing. Such particles can be formed from any biodegradable polymer not inconsistent with the objectives of the present disclosure. In some cases, the plurality of biodegradable polymer particles are formed from one or more polymers described hereinabove for the biodegradable polymer fibers of the wound dressing. For example, in some embodiments, the biodegradable polymer particles comprise or are formed from one or more of a polyester, polylactic acid, polyglycolic acid, polylactic-co-glycolic acid, polycaprolactone, and copolymers thereof.

The biodegradable polymer particles of a wound dressing described herein can also have any size and shape not inconsistent with the objectives of the present disclosure. In some embodiments, for example, the polymer particles are nanoparticles having an average size in one, two, or three dimensions of about 1000 nm or less. In some cases, the polymer particles have an average size in one, two, or three dimensions between about 1 nm and about 1000 nm, between about 1 nm and about 500 nm, between about 10 nm and about 1000 nm, between about 10 nm and about 500 nm, between about 10 nm and about 200 nm, between about 50 nm and about 1000 nm, between about 50 nm and about 500 nm, between about 100 nm and about 1000 nm, or between about 100 mu and about 500 nm. In other cases, the biodegradable polymer particles of a wound dressing described herein are microparticles having a size in one, two, or three dimensions greater than 1000 nm. In some embodiments, for instance, the polymer particles have an average size in one, two, or three dimensions between about 1 µm and about 100 µm, between about 5 µm and about 100 µm, between about 5 µm and about 50 µm, between about 10 µm and about 100 µm, between about 10 µm and about 50 µm, or between about 50 µm and about 100 µm. Moreover, in some cases, the polymer particles of a wound dressing described herein have an average size in one, two, or three dimensions that is smaller than the average diameter of the biodegradable polymer fibers of the wound dressing.

Further, the polymer particles of a wound dressing described herein can have a spherical or substantially spherical shape or a polygonal shape. Polymer particles described herein, in some cases, can also be rod-shaped. Other shapes are also possible.

Wound dressings described herein, in some embodiments, further comprise a second active agent dispersed in the polymer particles of the wound dressing. The second active agent can comprise any active agent not inconsistent with the objectives of the present disclosure. In some cases, the second active agent is selected to achieve a second biological effect, including a second biological effect that may desirably be temporally coupled with or at least partially separated from a first biological effect. For example, in some cases, the second biological effect could be the promotion of wound healing following the promotion of blood vessel growth. In other cases, the second biological effect could be the promotion of bone growth and development following the promotion of blood vessel growth. In some embodiments, the second active agent of a wound dressing described herein comprises a growth factor, including any growth factor described hereinabove for the first active agent of a wound dressing. In some cases, for instance, the second active agent comprises a growth factor for wound healing or bone growth. In other embodiments, the second active agent comprises an osteoinductive growth factor, such as transforming growth factor-β, or a bone morphogenetic protein (BMP).

A second active agent can be present in polymer particles of a wound dressing described herein in any amount not inconsistent with the objectives of the present disclosure. For example, in some cases, a second active agent is present in the particles in an amount up to about 20 weight percent, up to about 10 weight percent, up to about 5 weight percent, or up to about 1 weight percent, based on the total weight of the particles.

In another aspect, wound dressings described herein comprise a stack of biodegradable polymer fiber meshes. In some embodiments, the stack of meshes is arranged to provide a property gradient in the z-direction, where the z-direction is defined as the stacking direction or height of the stack. For example, in some cases, the meshes are porous meshes and the stack of meshes exhibits a porosity gradient in the z-direction. In some such embodiments, the porosity of the stack decreases from the bottom to the top of the stack. Alternatively, in other instances, the porosity of the stack increases from the bottom to the top of the stack.

Further, in some embodiments, one or more of the meshes of a stack described herein are perforated meshes and the stack of meshes exhibits a perforation gradient in the z-direction. In some such cases, the degree of perforation of the meshes decreases from the bottom to the top of the stack. In other instances, the degree of perforation of the meshes increases from the bottom to the top of the stack. Moreover, in some embodiments, the top mesh of a stack of meshes described herein is non-perforated, where the "top" mesh refers to the mesh farthest from the side of the stack to be placed in contact with a wound.

The "degree of perforation" of a mesh described herein can be based on the number of perforations or holes per unit area of a surface of the mesh, the average size of the perforations or holes, or the total area or volume of the perforations or holes. The "degree of perforation" can also be based on the shapes of the perforations or holes. In some embodiments, the perforations or holes of a perforated mesh described herein have an average size or diameter of at least about 10 µm, at least about 20 µm, at least about 30 µm, at least about 50 µm, at least about 100 µm, or at least about 150 µm. In some cases, the perforations or holes of a perforated mesh described herein have an average size or diameter between about 10 µm and about 10 mm, between about 10 µm and about 5 mm, between about 10 µm and about 1 mm, between about 50 µm and about 10 mm, between about 50 µm and about 5 mm, between about 50 µm and about 1 mm, between about 100 µm and about 10 mm, between about 100 µm and about 5 mm, or between about 100 µm and about 1 mm. Perforations having such sizes, in some cases, can provide sufficient space for regenerated tissue to grow into and penetrate the mesh during wound healing. Further, in some instances, the perforations or holes of a perforated mesh described herein have a pitch or average distance between perforations or holes of about 0.1 mm to about 10 mm or about 0.5 mm to about 5 mm, where the average distance between perforations or holes is based on the center-to-center distance between adjacent perforations or holes. In addition, in some embodiments, a perforated mesh described herein has a perforation or hole density of at least about 10 perforations/cm$^2$, at least about 20 perforations/cm$^2$, at least about 30 perforations/cm$^2$, at least about 50 perforations/cm$^2$, or at least about 70 perforations/cm$^2$, where the area is based on the total area of a perforated surface of the perforated mesh and where the average size of the perforations can be a size described herein, such as a size greater than about 50 μm. In some cases, a perforated mesh described herein has a perforation or hole density between about 10 perforations/cm$^2$ and about 200 perforations/cm$^2$, between about 20 perforations/cm$^2$ and about 150 perforations/cm$^2$, or between about 30 perforations/cm$^2$ and about 100 perforations/cm$^2$, wherein the average size of the perforations is a size described hereinabove.

A stack of perforated meshes having a porosity and/or perforation gradient described herein, in some cases, can permit improved penetration of cells from a wound site into the stack. In addition, a stack of meshes having a porosity and/or perforation gradient described herein, in some embodiments, can permit the gradual transfer of mechanical load from the stack of meshes to the tissue of the wound site as healing occurs. Specifically, wound dressings comprising a stack of meshes described herein, in some embodiments, can provide gradual transfer of mechanical loads from the mesh itself to regenerated biological tissue as wound healing progresses. Not intending to be bound by theory, it is believed that such gradual transfer of mechanical load, in some cases, can be achieved by the cell penetration afforded by perforations and perforation gradients described herein. Additionally, in some embodiments, a perforated mesh described herein can exhibit one or more mechanical properties provided in Table I below, when measured according to ASTM D412A.

TABLE I

Mechanical Properties of Perforated Meshes.

| Elongation at Break (%) | Initial Modulus (MPa) | Peak Stress (MPa) |
|---|---|---|
| >300 | >2 | >1 |
| >400 | >5 | >2 |
| >500 | >10 | >3 |
| 50-600 | 2-15 | 1-6 |
| 50-500 | 2-10 | 1-5 |
| 100-500 | 5-15 | 1-4 |
| 200-600 | 5-10 | 2-4 |
| 300-600 | 10-15 | 3-5 |

A wound dressing comprising a stack of meshes described herein can include any number of meshes not inconsistent with the objectives of the present disclosure. In some cases, for example, a wound dressing comprises at least two, at least three, at least five, at least 10, or at least 20 meshes in a stacked configuration. In some instances, a wound dressing comprises up to 50 or up to 100 meshes in a stacked configuration. Further, the meshes of such a wound dressing can independently have any structure or property of a mesh described herein.

For example, in some embodiments, a wound dressing described herein comprises a first perforated mesh formed from a first plurality of biodegradable polymer fibers; and a second perforated mesh formed from a second plurality of biodegradable polymer fibers, wherein the second perforated mesh is disposed on the first perforated mesh in a stacked configuration and the first perforated mesh has a higher degree of perforation than the second perforated mesh. Moreover, in some cases, a wound dressing further comprises a third perforated mesh formed from a third plurality of biodegradable polymer fibers, wherein the third perforated mesh is disposed on the second perforated mesh in a stacked configuration and the third perforated mesh has a higher degree of perforation than the first perforated mesh and the second perforated mesh. Additionally, if desired, wound dressings described herein can further comprise additional perforated meshes or non-perforated meshes in a stacked configuration.

For example, in some embodiments, the top mesh of a wound dressing described herein is a non-perforated mesh. Thus, in some cases, a wound dressing described herein further comprises a fourth mesh formed from a fourth plurality of biodegradable polymer fibers, wherein the fourth mesh is disposed on the third perforated mesh in a stacked configuration and the fourth mesh is non-perforated or has a lower degree of perforation than the third perforated mesh. A wound dressing having such a structure, in some cases, can provide a physical barrier to complete tissue penetration of the wound dressing on the side of the wound dressing farther from the wound.

As described above, it is generally to be understood that the number of stacked meshes in a wound dressing described herein is not particularly limited. Instead, any desired number of meshes can be used to provide a wound dressing having a desired thickness and/or a desired property gradient in the z-direction. The meshes of a stack described herein can also be arranged to provide a wound dressing having regularly or irregularly repeating properties in the z-direction. In some cases, for instance, the meshes of a stack described herein have alternating hydrophobicity and hydrophilicity. Thus, in some embodiments, a wound dressing described herein comprises a first perforated mesh and a second perforated mesh in a stacked configuration, wherein the first perforated mesh is hydrophilic and the second perforated mesh is hydrophobic. Other arrangements of meshes are also possible.

Additionally, one or more meshes of a stack described herein can have a structure described hereinabove for wound dressings comprising active agents. For example, in some cases, one or more active agents are dispersed in the biodegradable polymer fibers of a first perforated mesh and/or a second perforated mesh of a stack described herein. Further, in some embodiments, a plurality of biodegradable polymer particles is disposed in a first perforated mesh and/or a second perforated mesh of a wound dressing described herein. Moreover, in such cases, one or more second active agents can be dispersed in the biodegradable polymer particles. The first and second active agents of such a wound dressing can comprise any first active agent, second active agent, and combination of first and second active agents described hereinabove. In some embodiments, for instance, the in vivo or in vitro release profile of a first active agent of a stack differs from the in vivo or in vitro release profile of a second active agent of the stack. In such cases, the in vivo or in vitro release profiles of the active agents can differ in a manner described hereinabove. For example, in some cases, the in vivo or in vitro release profile of the first active agent and the in vivo or in vitro release profile of the second active agent of a stack of meshes described herein overlap by less than about 70%. In other cases, the release profiles are entirely non-overlapping.

In addition, wound dressings described herein, in some embodiments, can also include one or more electrically conductive components for neural and muscular tissue engineering applications. For example, in some cases, the mesh of a wound dressing described herein further comprises one or more electrically conductive polymer fibers, such as one or more fibers formed from polypyrrole, polyaniline, or a polythiophene such as poly(3,4-ethylendioxythiophene) (PEDOT). Similarly, in some instances, a wound dressing described herein can comprise a plurality of electrically conductive polymer particles, such as polyaniline particles, polypyrrole particles, or PEDOT particles. Other electrically conductive polymer fibers and particles can also be used. Such electrically conductive polymer fibers and particles can be used in addition to the components of biodegradable wound dressings described herein or in place of such components. For example, in some instances, a wound dressing described herein comprises a mesh formed from a plurality of electrically conductive polymer fibers and a plurality of electrically conductive polymer particles disposed in the mesh. The particles can be disposed between the fibers of the mesh or within the fibers of the mesh. Further, in some cases, one or both of the electrically conductive polymer fibers and the electrically conductive polymer particles comprise an active agent. In some embodiments, for instance, the electrically conductive polymer fibers and the electrically conductive polymer particles comprise a combination of first and second active agents described herein.

Various components of compositions and wound dressings have been described herein. It is to be understood that a composition or wound dressing according to the present disclosure can comprise any combination of components and features not inconsistent with the objectives of the present disclosure. For example, in some cases, a wound dressing described herein comprises any mesh described herein in combination with any polymer particles described herein and any active agents described herein.

Wound dressings having a structure described hereinabove can be made in any manner not inconsistent with the objectives of the present disclosure. For example, in some embodiments, a wound dressing described herein is made by an electrospinning process. In some cases, such a method of making a wound dressing comprises electrospinning a mixture comprising a first biodegradable polymer, a first solvent, and a first active agent such as a first growth factor. Electrospinning such a mixture can provide a plurality of polymer fibers formed from the first biodegradable polymer, wherein the first active agent is dispersed within the polymer fibers. Further, as described further hereinbelow, the electrospinning process can form the polymer fibers into a non-woven mesh. In addition, in some embodiments, the mixture for electrospinning can further comprise a plurality of biodegradable polymer particles described herein. Electrospinning such a mixture can provide a mesh described herein, wherein the polymer particles are dispersed within the polymer fibers. In some such cases, the solvent of the mixture is selected for its compatibility with the biodegradable polymers of the fibers and/or particles and for its compatibility with the first and/or second active agents. For example, in some embodiments, the first biodegradable polymer is soluble in the solvent of the mixture but the biodegradable polymer particles are not soluble in the solvent. In some such cases, for instance, an aqueous solvent is used with a water-soluble first biodegradable polymer and with hydrophobic polymer particles.

Alternatively, a plurality of biodegradable polymer particles can be disposed in between fibers of a mesh by forming a mesh of polymer fibers in a manner described hereinabove, followed by treating the mesh with a solution or mixture comprising the polymer particles. For example, in some cases, a particle solution or mixture can be drop cast onto the mesh. The mesh can also be immersed in the particle solution or mixture.

Similarly, electrospinning may also be used to provide a wound dressing comprising a stack of meshes described herein. Such a method, in some embodiments, comprises forming a plurality of meshes in a manner described hereinabove and then stacking the meshes. In addition, in some cases, one or more of the meshes are perforated before or after stacking the meshes to provide the wound dressing. As described further hereinbelow, multiple meshes can be stacked in any manner not inconsistent with the objectives of the present disclosure. In some cases, for example, multiple meshes can be stacked by directly electrospinning different meshes one on top of the other, by physically pressing meshes together, by applying a biodegradable adhesive between adjacent meshes, or by applying mild solvent for surface welding adjacent meshes. Other stacking techniques may also be used.

II. Methods of Treating a Wound

In another aspect, methods of treating a wound are described herein. In some embodiments, a method of treating a wound comprises applying a composition or wound dressing described herein to a surface of a wound. Any composition or wound dressing described hereinabove in Section I may be used. In some cases, for instance, a wound dressing comprises a mesh formed from a plurality of biodegradable polymer fibers; a first active agent dispersed in the biodegradable polymer fibers; a plurality of biodegradable polymer particles disposed in the mesh; and a second active agent dispersed in the biodegradable polymer particles. Further, in some instances, the particles are disposed within the fibers of the mesh. Additionally, a method comprising the application of such a wound dressing, in some cases, can further comprise at least partially degrading the biodegradable polymer fibers to release the first active agent into the wound. Degrading the polymer fibers, in some cases, comprises cleaving one or more chemical bonds such as one or more ester bonds in the polymer fibers. Moreover, degrading the polymer fibers of a wound dressing can, in some embodiments, provide an in vivo release profile of the first active agent that corresponds to an in vivo release profile described hereinabove in Section I.

In addition, in some cases, a method described herein further comprises at least partially degrading the biodegradable polymer particles to release the second active agent into the wound. Degrading the polymer particles can comprise cleaving one or more chemical bonds in the particles, including one or more ester bonds. Further, degrading the polymer particles of a wound dressing in a manner described herein can provide an in vivo release profile of the second active agent that corresponds to an in vivo release profile described hereinabove in Section I. In some cases, for instance, the second active agent is released from the wound dressing after the first active agent is released from the wound dressing. Thus, as described further herein, a method of treating a wound described herein can comprise using a single wound dressing to provide a plurality of active agents to a wound site in a temporally controlled and/or bifurcated manner. For example, in some cases, the first active agent of a method described herein comprises a growth factor for angiogenesis, and the second active agent of the method comprises a growth factor for wound healing or bone growth.

In other embodiments of methods described herein, the composition or wound dressing applied to a wound comprises a stack of meshes. Such a composition or wound dressing can comprise any wound dressing described hereinabove in Section 1. For example, in some instances, the wound dressing comprises a first perforated mesh formed from a first plurality of biodegradable polymer fibers; and a second perforated mesh formed from a second plurality of biodegradable polymer fibers, wherein the second perforated mesh is disposed on the first perforated mesh in a stacked configuration and the first perforated mesh has a higher degree of perforation than the second perforated mesh.

In addition, a method described herein can be used to treat any type of wound not inconsistent with the objectives of the present disclosure. In some embodiments, for instance, the wound comprises a skin wound. In some cases, the wound comprises a diabetic ulcer or hernia.

Some embodiments described herein are further illustrated in the following non-limiting examples.

Example 1

Wound Dressings

Wound dressings according to some embodiments described herein were provided and used to treat wounds as follows.

Materials

Chitosan (CS, medium molecular weight, 75-85% deacetylated), polyethylene oxide (PEO, $M_n$=600,000 Dalton), bovine serum albumin (BSA), acetic acid, and chloroform were purchased from Sigma Aldrich (St. Louis, Missouri). Poly-lactic-co-glycolic acid (PLGA) (50:50) was purchased from Lakeshore Biomaterials (Birmingham, Alabama). Platelet Derived Growth Factor-BB (PDGF-BB, Human Recombinant) and Vascular Endothelial Growth Factor (VEGF, Rat Recombinant) were purchased from Prospec (East Brunswick, New Jersey). HDF (Adult Human Dermal Fibroblast) cells were purchased from ATCC (Manassas, Virginia). Gram-negative *Escherichia coli* (*E. coli*, 25922™) and gram-positive *Staphylococcus aureus* (*S. aureus*, 25923™) were also obtained from ATCC.

Biodegradable Polymer Particles

PLGA nanoparticles were fabricated using the double-emulsion technique described by Menon et al., "Effects of surfactants on the properties of PLGA nanoparticles," *Journal of Biomedical Materials Research, Part A*, 2012, 100, 1998-2005. Briefly, 200 µL of 5% w/v BSA or 2% w/v PDGF-BB aqueous solution was added to 3.33 mL of 3% w/v PLGA aqueous solution and sonicated at 30 W for 2 minutes. This o/w solution was then added dropwise to 12 mL 2% PVA solution and sonicated at 20 W for two minutes. This final w/o/w solution was then de-solvated overnight using a magnetic stirrer. Centrifugation was then performed at 4,000 rpm for 5 minutes to remove particle aggregates. The BSA or PDGF-BB loaded PLGA nanoparticles were obtained via freeze-drying. In addition, the supernatant from the nanoparticle formation process was also collected to determine the loading efficiency.

Biodegradable Polymer Mesh

A polymer mesh was prepared by electrospinning. First, stock polymer solutions were prepared. Specifically, a solution of chitosan (CS) at a concentration of 2.5% w/v was prepared in 90% acetic acid. A solution of PEO at a concentration of 8% w/v was prepared in deionized (DI) water at room temperature. Next, two CS/PEO blend solutions were prepared by mixing the two stock solutions at 1:1 and 2:1 chitosan to PEO volume ratios. For reference purposes, polymer fibers formed from these mixtures, without nanoparticles, are denoted as 1:1 CS/PEO and 2:1 CS/PEO, respectively. To provide polymer fibers comprising nanoparticles, 20% by weight of PLGA nanoparticles (based on the weight of PEO) was added to the CS/PEO mixtures and sonicated for 10-15 minutes at 20 W to obtain complete or substantially complete dispersion of the nanoparticles. These fibers were denoted as 1:1 CS/PEO-NPs and 2:1 CS/PEO-NPs.

For electrospinning, each of the blended solutions above was individually loaded into a 5 mL syringe equipped with an 18-gauge blunt needle tip. For each electrospinning experiment, the syringe was loaded into a syringe pump. The contents of the syringe were delivered for electrospinning by driving the syringe plunger with the syringe pump at a flow rate of 1.5 µL/min. The tip of the syringe was disposed 15 cm away from an aluminum mesh collector, and a DC voltage of 18 kV was applied between the collector and the tip. All electrospinning experiments were carried out at ambient temperature (about 25° C.) and a relative humidity of 15-20%.

Results

The surface morphology of the electrospun nanofiber mesh was characterized using a scanning electron microscope (SEM) (Hitachi, S-3000N). All samples were first sputter-coated with silver. Fiber diameters were determined from SEM images using Image-J software. For each mesh, 100 fibers were considered from three different images to calculate the average diameter. To visualize the nanoparticles within the nanofibers, indocyanine green (ICG) loaded PLGA nanoparticles were prepared and electrospun. Fluorescent images were captured using a fluorescence microscope equipped with a TRITC filter.

To assess the active agent release kinetics, BSA was selected as a model protein. Specifically, BSA was incorporated into the biodegradable polymer fibers and/or the biodegradable polymer particles in the manner described above. Meshes containing BSA and weighing 10.0-11.0 mg were loaded into 100-kDa dialysis membranes and placed in 0.1 M phosphate buffered saline (PBS) solutions. The samples were then placed on an orbital shaker at 37° C. At predetermined time points, 1 mL of PBS solution was collected and replaced with 1 mL fresh PBS. The release profile of BSA (60 kDa), either from the nanofibers themselves or from PLGA nanoparticles within the nanofibers, was analyzed using standard BSA protein assays following the manufacturer's instructions. Cumulative release over a period of 21 days was performed on all samples.

Adult Human Dermal Fibroblasts (HDFs) were cultured in complete Dulbecco's Modified Eagle's medium (DMEM) with supplements of 10% Fetal Bovine Serum (FBS) and 1% penicillin/streptomycin solution. Cells were sub-cultured until approximately 80% confluency and maintained at a humidified atmosphere of 95% air and 5% $CO_2$. For in vitro cell proliferation on nanofiber meshes, mesh samples (3 mm in diameter) were vacuum dried overnight and then UV-sterilized for 1 hour. Samples were then placed in a 96-well plate and seeded with 5000 cells/well. A tissue culture plate was used as a control. MTS assays were performed at time points of 1, 3, 5, and 7 days following seeding. Absorbance at 490 nm was measured, and the cell proliferation was plotted over time as a percentage over the control sample at day 1.

To assess the antibacterial activity of the samples, three types of nanofiber meshes were used. Specifically, 1:1 CS/PEO, 2:1 CS/PEO, and 2:1 CS/PEO-NPs were used. All mesh samples were vacuum-dried and UV sterilized. 20 mg of each type of mesh were used. *E. coli* and *S. aureus* were reconstituted based on the supplier's instructions. A bacteria suspension and PEO nanofibers without chitosan were chosen as the negative controls for antibacterial activity. Penstrep was used as the positive control. For each sample, a bacterial suspension was prepared at an optical density (OD) of 0.011 at 600 nm (measured by a UV-vis spectrophotometer), added to the sample, and incubated at 37° C. After incubation, the absorbance at 600 nm of each sample was measured at predetermined time points. The average of background samples was subtracted from the test samples and plotted over time. All operations were carried out in aseptic conditions.

Sprague-Dawley rats weighting approximately 250 g were used for in vivo studies. Specifically, full thickness skin wound healing studies were carried out. All animals were treated and used in accordance with the protocol approved by the University of Texas at Arlington Animal Care and Use Committee (IACUC). Animals were anesthetized with ketamine (40 mg/kg) and xylazine (5 mg/kg), and then shaved on the back. A 5 mm diameter biopsy puncher was used to create a wound along the dorsal side of the skin. Four wounds were created on each rat, and then controls (open wound and Hydrofera Blue®) and the test samples were placed on the wound site randomly. Changes in the wound areas were measured using a caliper at 1, 7, 14, and 28 days after initial wounding and placement of the wound dressings. At each time point, the surrounding skin and muscle including wound areas were removed and fixed by 10% neutral buffed formalin. Tissue samples were embedded in paraffin and sectioned. Hematoxylin-eosin (H&E) and Masson's Trichrome staining were performed to evaluate the skin tissue sections.

Physical measurements of surface epidermal tongue and granulation tissue thickness of the H&E images were measured using Image-J. Collagen quantification was carried out by measuring the blue area percentage of the wound area with Masson's Trichrome staining.

All data herein is presented as the mean±standard deviation (SD). Statistical analysis of all data was performed using 1-way ANOVA (StatView), where p values <0.05 were considered statistically significant (n=6).

FIG. 1 is a schematic illustration of an exemplary wound dressing (100) described herein and a method of treating a wound (200) using the wound dressing (100). As illustrated in FIG. 1, PDGF-BB (140) was encapsulated within PLGA nanoparticles (130) (average diameter of 153±36 nm, as determined by Dynamic Light Scattering) of the wound dressing (100), and then dispersed in CS/PEO nanofibers (110). In addition, VEGF (120) was loaded into the nanofibers (110) of the mesh. The wound dressing (100) was then applied to the wound (200). Following application of the wound dressing (100) to the wound (200), the relatively fast-releasing VEGF (120) and the relatively slow- or sustained-releasing PDGF-BB (140) were released into the wound (200) to promote wound healing.

FIG. 2 illustrates SEM images of various meshes described herein having the structure illustrated in FIG. 1. FIG. 2A corresponds to 2:1 CS/PEO-NPs. FIG. 2B corresponds to 1:1 CS/PEO-NPs. The SEM images show smooth, uniform, and headless fibrous nonwoven structures. The 1:1 CS/PEO-NPs mesh had a smaller average fiber diameter of 116±39 nm, while the 2:1 CS/PEO-NPs mesh had an average fiber diameter of 132±39 nm. In order to visualize the nanoparticles within the fibers, PLGA nanoparticles were loaded with indocyanine green (ICG) and imaged by fluorescence microscopy. FIG. 2C is a fluorescence image of ICG loaded NPs in CS/PEO fibers. As shown in FIG. 2C, the nanoparticles were located within fibers and were uniformly distributed. FIG. 2D illustrates diameter distributions of the electrospun fibers of the samples.

Figure 3:
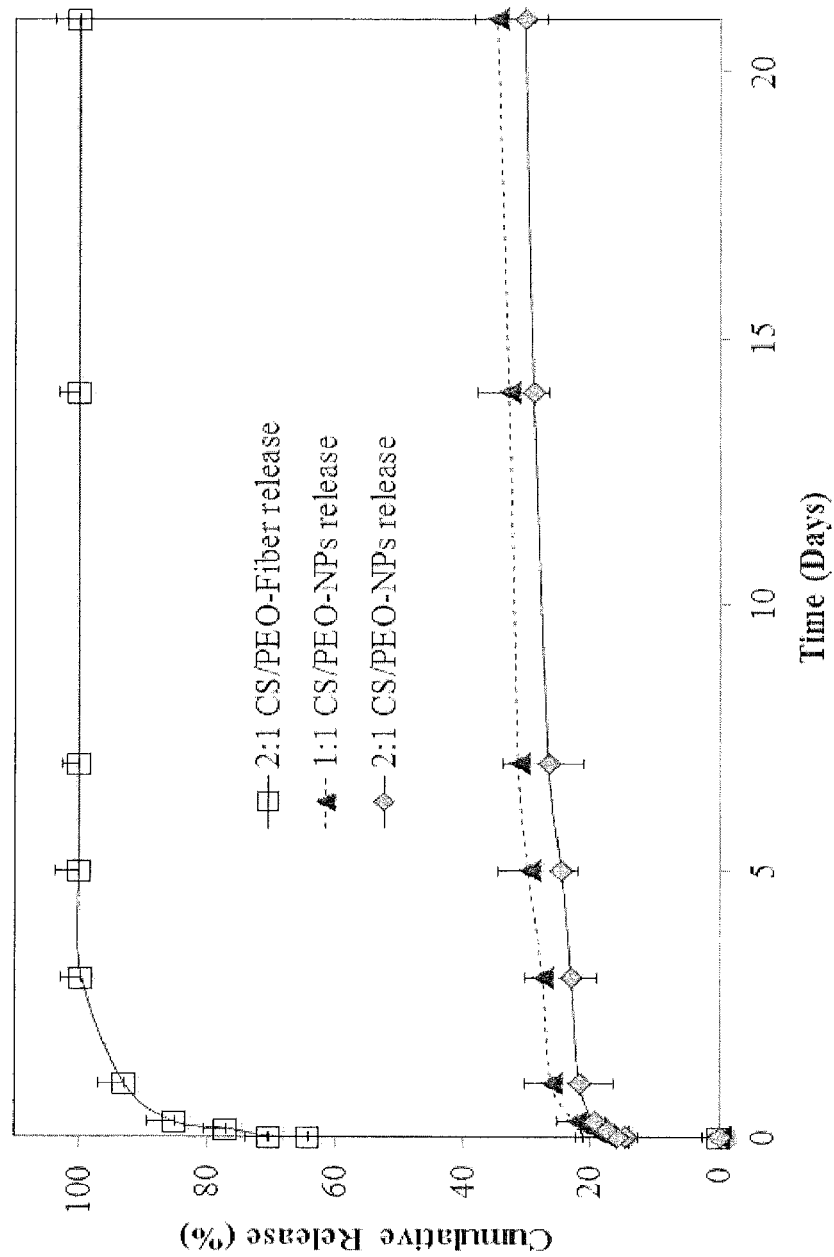
FIG. 3 illustrates plots of the release profiles of active agents of wound dressings according to some embodiments described herein.

FIG. 3 illustrates BSA release kinetics from nanofibers and nanoparticles within fibers. For reference purposes, the nomenclature "Fiber" and "NPs" is used to indicate which portion of the mesh was loaded with BSA. For example, the 2:1 CS/PEO-Fiber release profile corresponds to BSA loaded into the nanofibers only, and the 1:1 CS/PEO-NPs and 2:1 CS/PEO-NPs release profiles correspond to BSA loaded into PLGA nanoparticles that were encapsulated in the nanofibers, and wherein no BSA was dispersed in the nanofibers themselves. As illustrated in FIG. 3, BSA was released from nanofibers quickly. For example, the 2:1 CS/PEO-Fiber release profile included an initial burst release of 64% within the first 30 minutes. The BSA loaded within the 2:1 CS/PEO mesh was all released by day 3. In contrast, BSA released from PLGA nanoparticles within a 2:1 CS/PEO-NPs mesh showed only a small initial burst release of 16% at day 1. In addition, BSA release from PLGA nanoparticles for both meshes exhibited a sustained release pattern.

Figure 4:
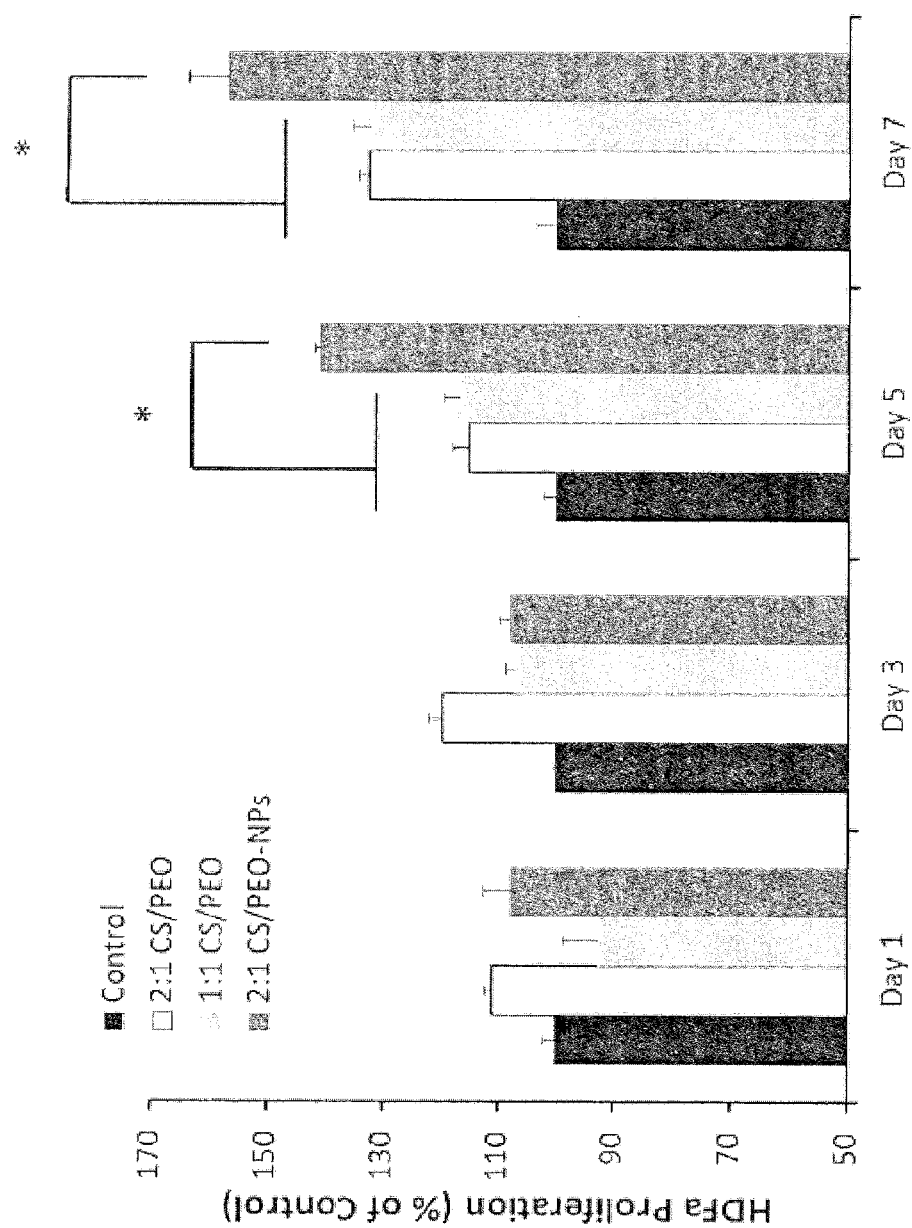
FIG. 4 illustrates plots of cell proliferation following treatment of a wound according to some embodiments described herein.

FIG. 4 illustrates the results of cell proliferation experiments for the following sample meshes: 1:1 CS/PEO, 2:1 CS/PEO, and 2:1 CS/PEO-NPs (PLGA nanoparticles loaded with PDGF-BB). Meshes were seeded with HDFs and MTS assay was used to quantify the cell viability (*p<0.01). All of the PEO/CS meshes were cytocompatible throughout the time period of the experiment and exhibited more cell growth than the control. Cell proliferation was significantly increased on days 5 and 7 on all meshes compared to the control. A growth of 116.91±2.9% was observed on 1:1 CS/PEO on day 5, and 115.2±2.8% growth was observed on the 2:1 CS/PEO mesh. On day 7, the 1:1 CS/PEO growth was 132.6±1.8%, and a proliferation of 132.5±2.9% was observed for 2:1 CS/PEO. The CS/PEO-NPs sample with PDGF-BB loaded nanoparticles exhibited significantly faster cell growth for day 5 (140.9±0.8%) and day 7 (156.8±6.6%) compared to the tissue culture plate control.

Figure 5A:
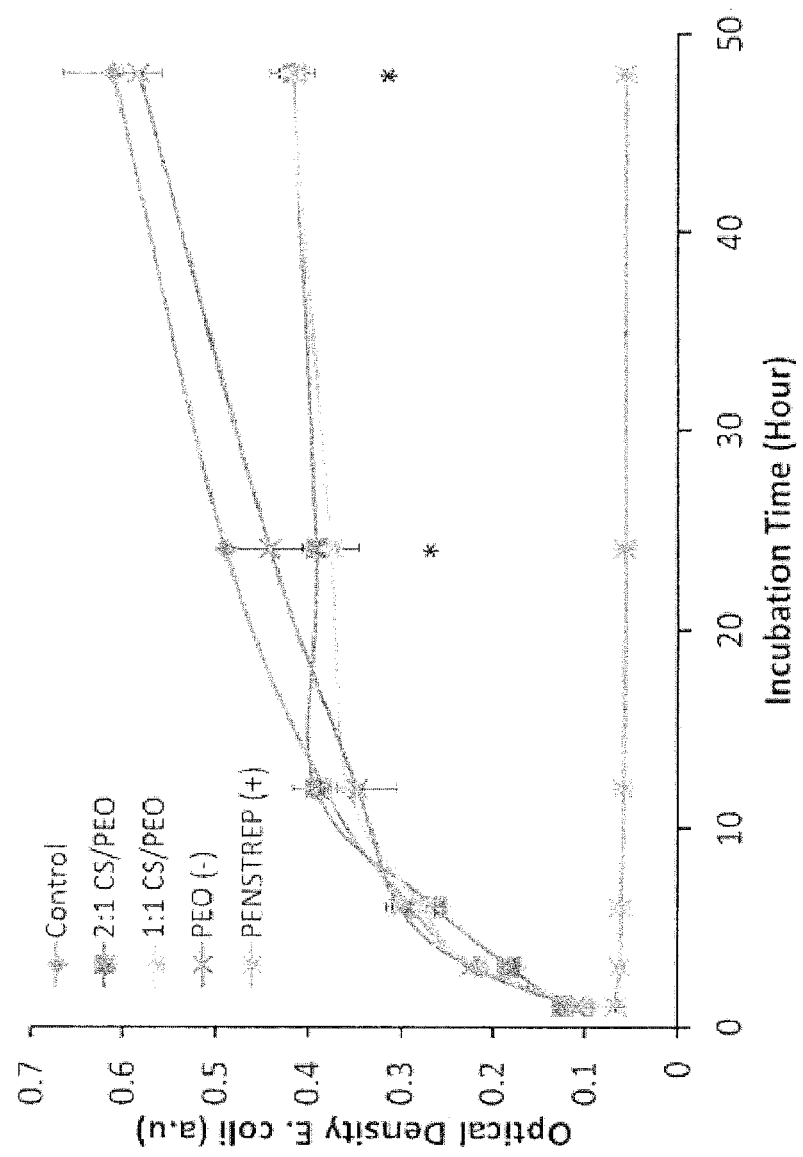
FIGS. 5A and 5B illustrate plots of the antimicrobial properties of wound dressings according to some embodiments described herein.
Figure 5B:
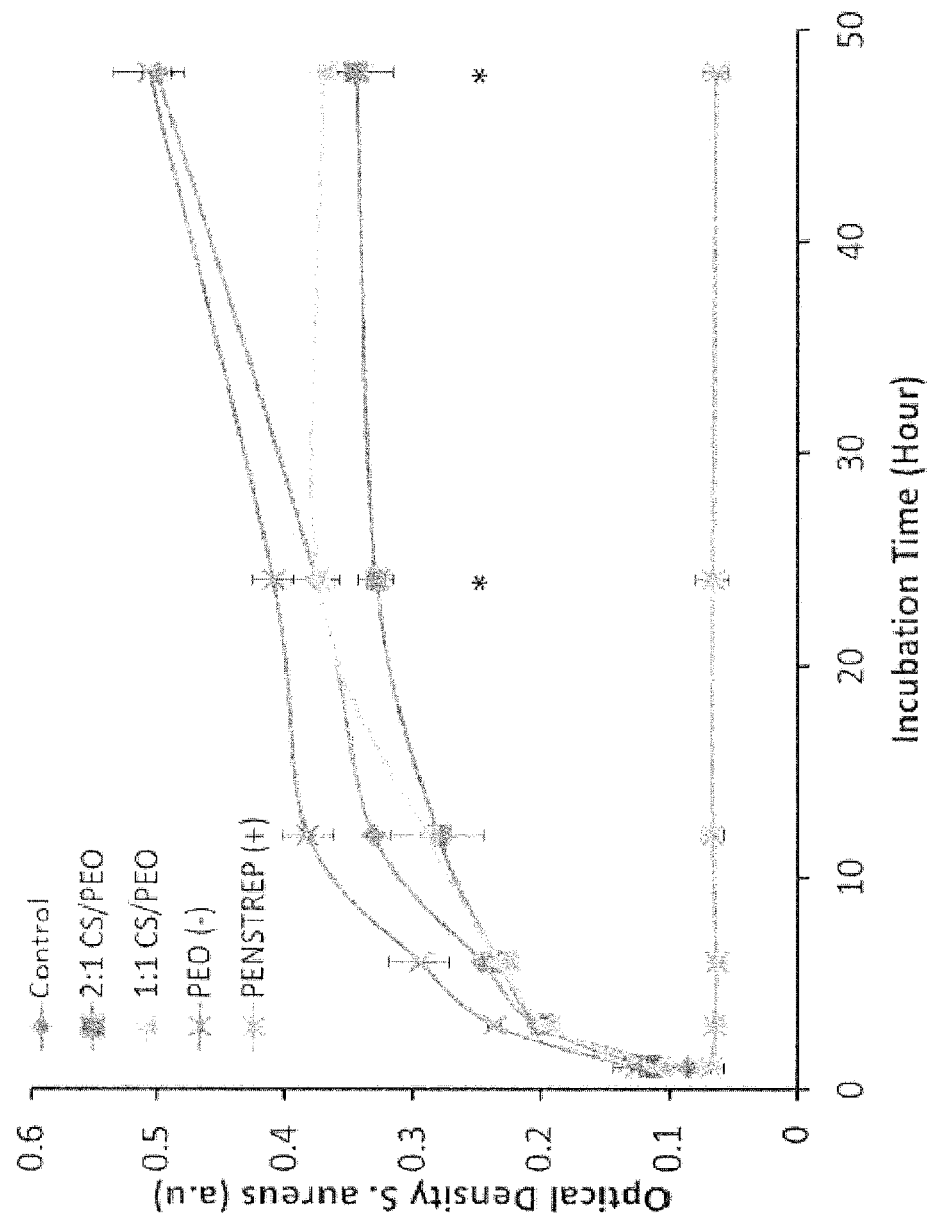

FIG. 5 illustrates antibacterial properties of various CS/PEO-NPs meshes compared to negative controls (cell suspension and PEO mesh) and a positive control (Penstrep solution). Antibacterial activity was assessed based on bacterial optical density, as described above. Two types of bacteria, *E. coli* (FIG. 5A) and *S. aureus* (FIG. 5B) were used. As illustrated in FIG. 5, the negative controls showed continuous expansion of both *E. coli* and *S. aureus*. In contrast, 1:1 CS/PEO-NPs and 2:1 CS/PEO-NPs meshes exhibited antibacterial activity against both *E. coli* and *S. aureus* compared to negative controls (*p<0.05).

FIG. 6 illustrates wound healing properties of various meshes described herein. Specifically, FIG. 6A illustrates representative macroscopic appearances of wound closures at 0, 1, 2, and 4 weeks after treatment of skin wounds. Electrospun 2:1 CS/PEO-NPs without growth factor (denoted as 2:1 CS/PEO in FIGS. 6-8) and 2:1 CS/PEO-NPs with VEGF in the fibers and PDGF-BB in PLGA nanoparticles (denoted as 2:1 CS/PEO-NPs in FIGS. 6-8) were placed and adhered on the wound site easily. Further, compared to commercial Hydrofera Blue, which requires biological adhesives to be fixed on a wound site, the meshes were much easier to attach to wounds. In addition, approximately 4 hours after placement, the meshes became invisible to the eye. At 1 week after treatment, no infection was observed for all samples. Higher granulation and regenerated epidermis were observed for 2:1 CS/PEO-NPs meshes, as confirmed later by histological analysis. At 2 weeks after treatment, scabs fell from the skin wounds for all samples. Again, 2:1 CS/PEO-NPs samples exhibited faster healing with more regenerated skin and more hair growth. After 4 weeks, all wounds appeared to be closed. Scabs were observed on Hydrofera Blue samples only.

Figure 6B:
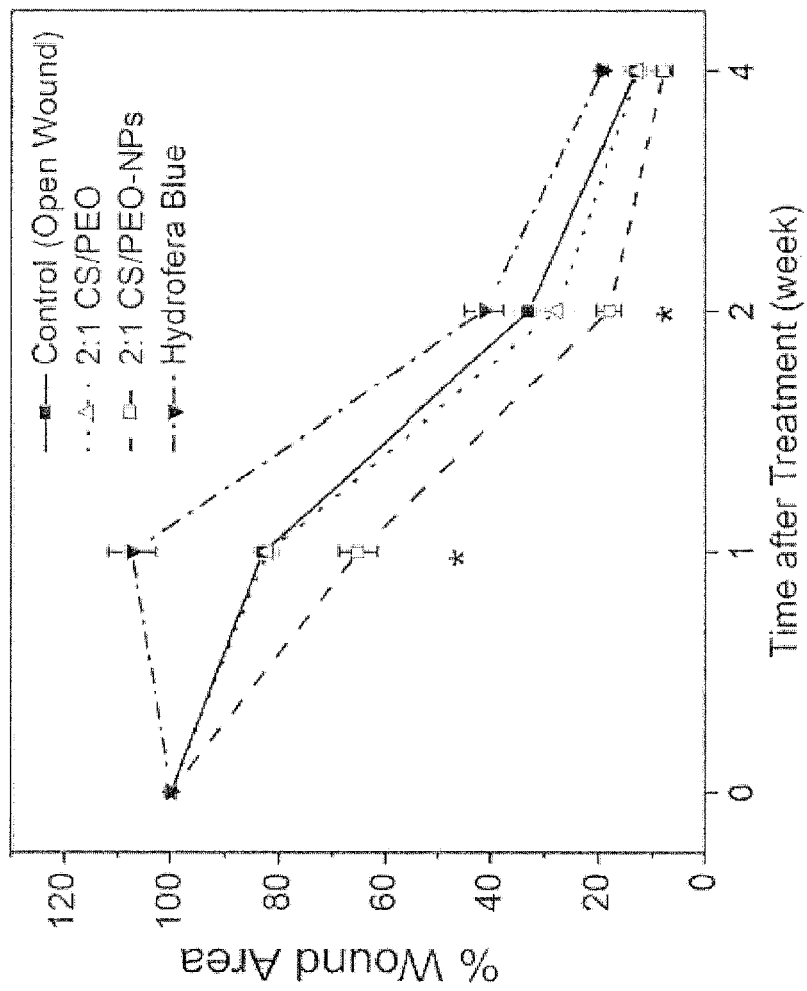
FIG. 6B illustrates plots of wound healing as a function of time according to some embodiments of methods described herein.
Figure 7A:
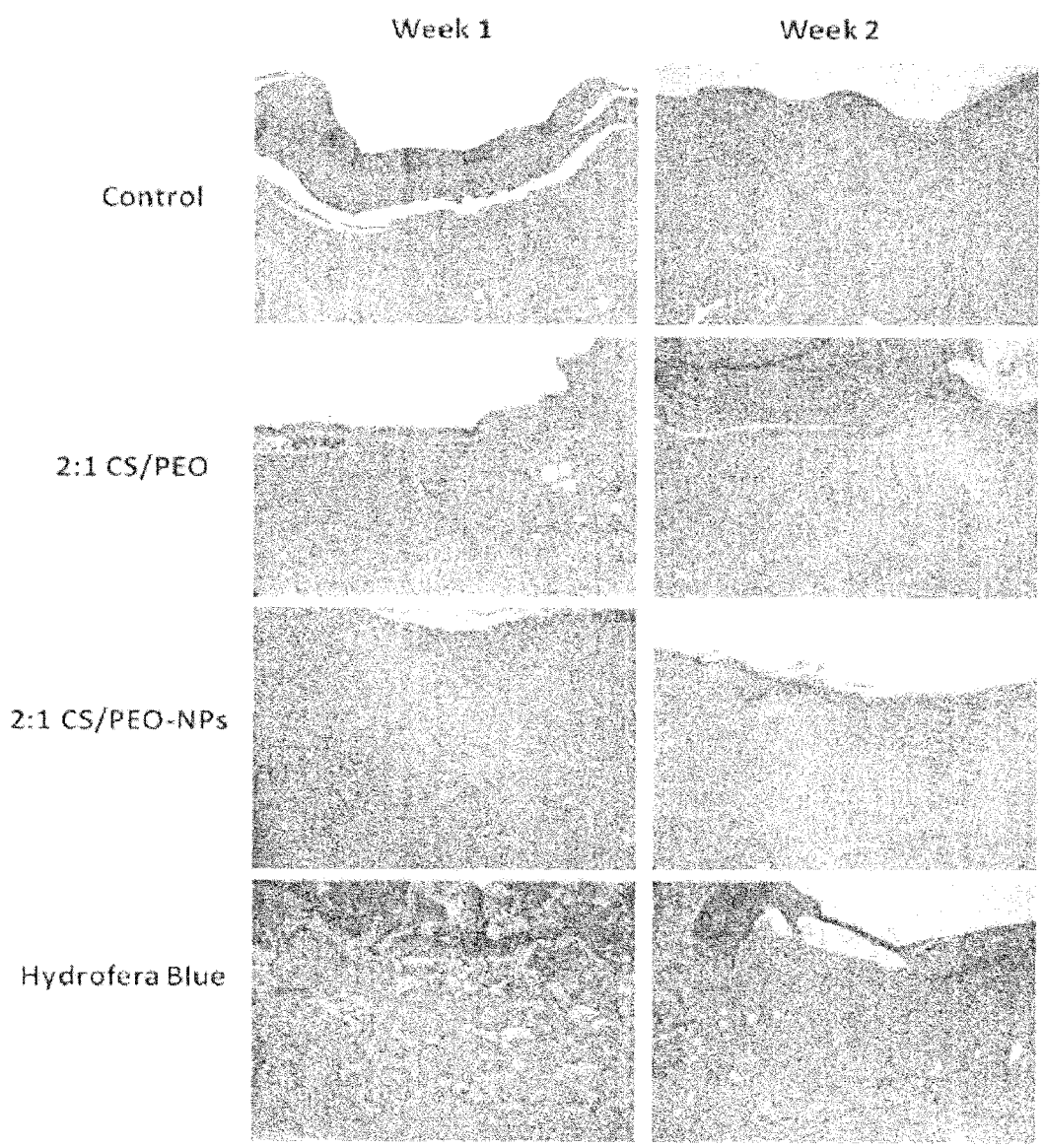
FIG. 7A illustrates staining images of wounds treated according to some embodiments of methods described herein.
Figure 7B:
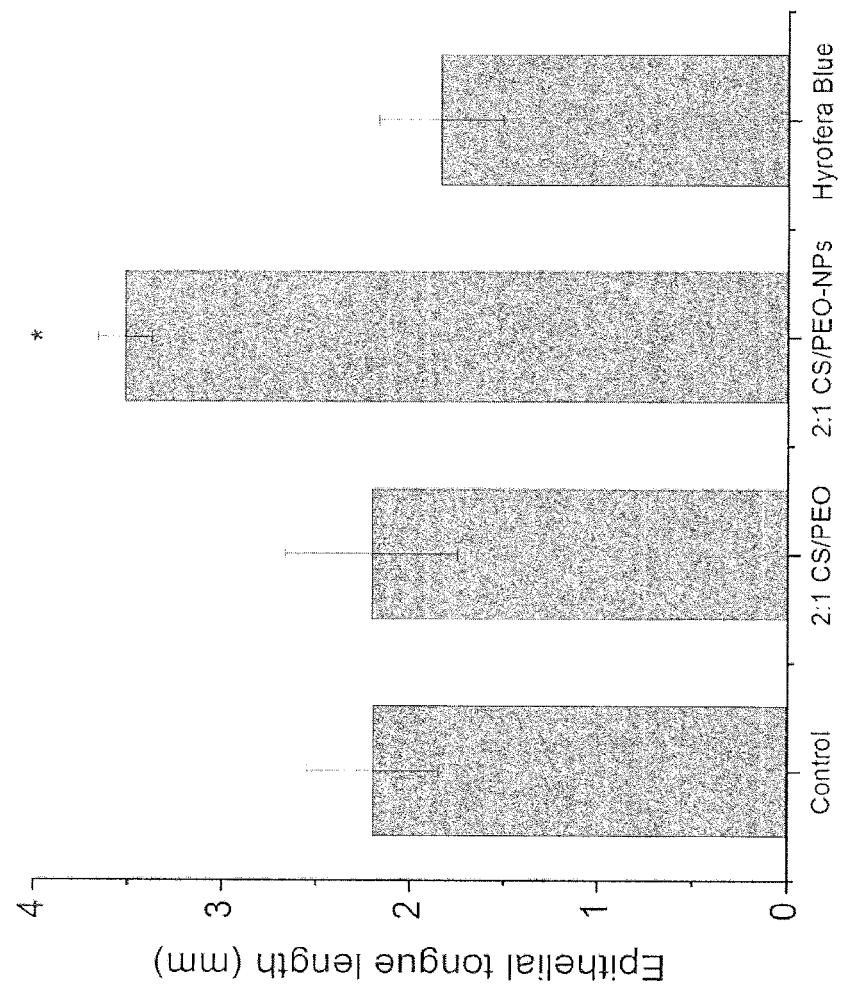
FIGS. 7B-7D illustrate plots of the results of treating a wound according to some embodiments of methods described herein.
Figure 7C:
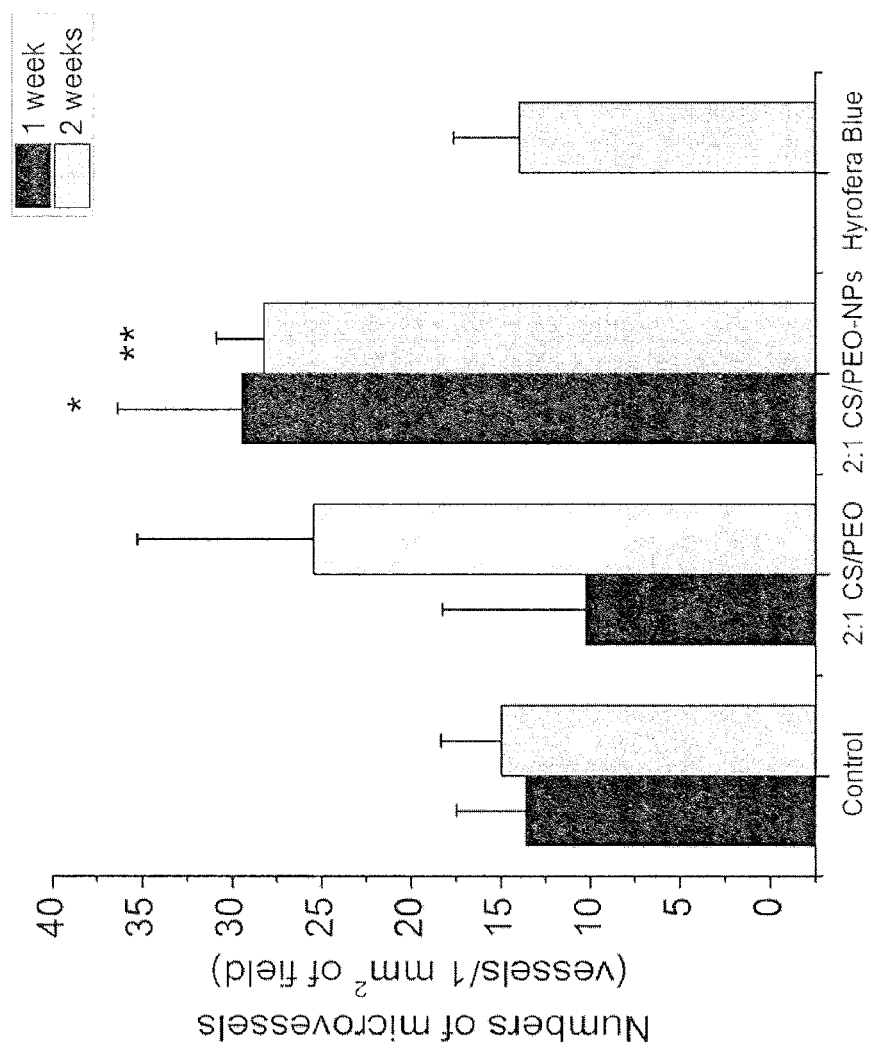
Figure 7D:
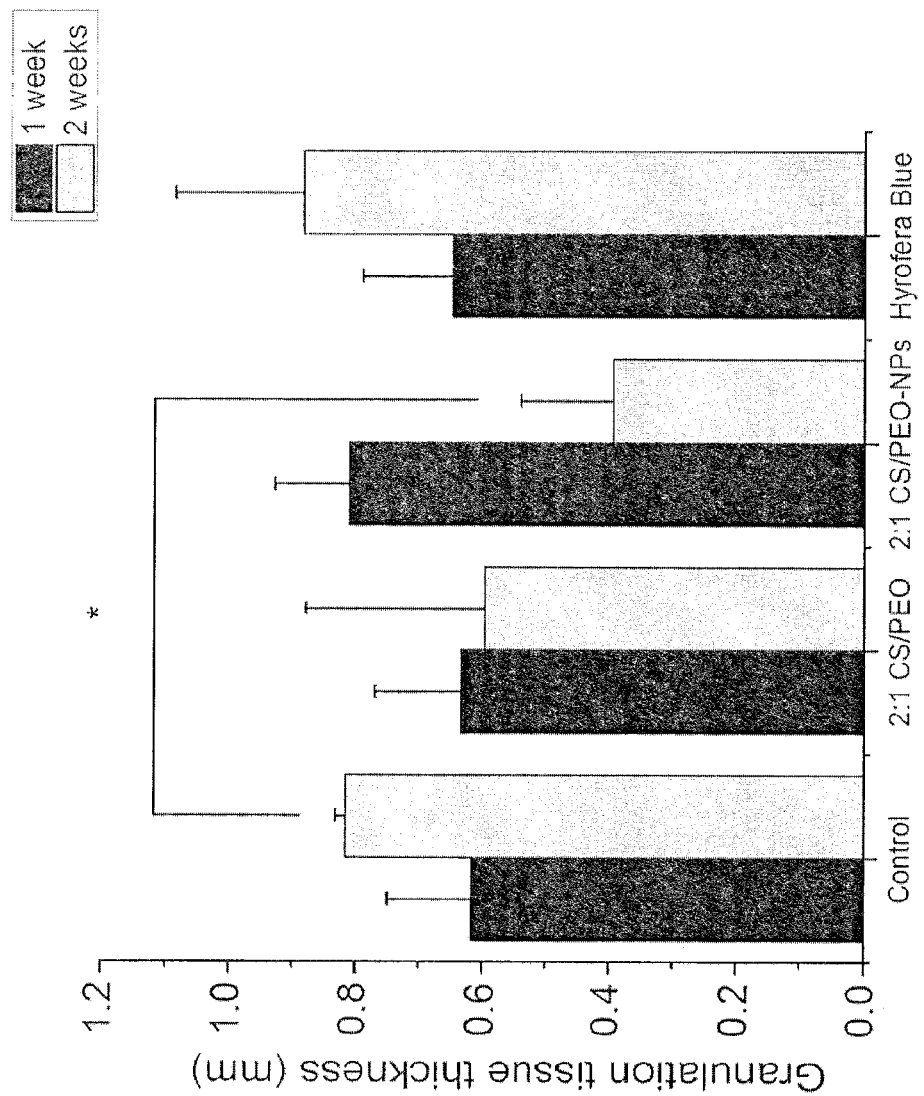

FIG. 6B illustrates quantitative measurements of wound size reduction or wound closure as a function of time (*p<0.01). As illustrated in FIG. 6B, wound areas for 2:1 CS/PEO-NPs meshes were significantly smaller than those of other samples at weeks 1 and 2 (p<0.05). It was also observed that at week 1 Hydrofera Blue exhibited a slightly increased wound size due to extensive scar formation. After 4 weeks of treatment, all wounds were closed. 2:1 CS/PEO-NPs exhibited the smallest scar formation area and the greatest hair coverage.

FIG. 7 illustrates the results of histological evaluation of the wounds treated by CS/PEO-NPs meshes and Hydrofera Blue wound dressing. FIG. 7A illustrates H&E staining for skin wound samples of control (open wound), 2:1 CS/PEO, 2:1 CS/PEO-NPs, and Hydrofera Blue samples after 1 and 2 weeks of treatment. FIG. 7B illustrates epithelial tongue length after 1 week of treatment. FIG. 7C illustrates the capillary density at wound sites after 1 and 2 weeks of treatment. FIG. 7D illustrates granulation tissue thickness after 1 and 2 weeks of treatment. (*, **p<0.05). Longer epithelial tongues were observed for 2:1 CS/PEO-NPs samples (FIG. 7B). At one week and two weeks, significantly more newly formed capillaries within the wound site were observed for 2:1 CS/PEO-NPs compared to open wound (p<0.01) (FIG. 7C). After 2 weeks of treatment, full coverage of new epithelium was identified for all samples except the Hydrofera Blue samples. In addition, with a complete closure of epithelium, rapid clearance of PEO, and sustained release of PDGF-BB, the granulation tissue thickness for 2:1 CS/PEO-NPs at week 2 was significantly reduced compared to that of week 1 and open wound control (p<0.01), suggesting a transition from Phase I (inflammation) to Phase II (proliferation) of the healing process (FIG. 7D). The control and Hydrofera Blue samples exhibited thicker layers of granulation.

Figure 8A:
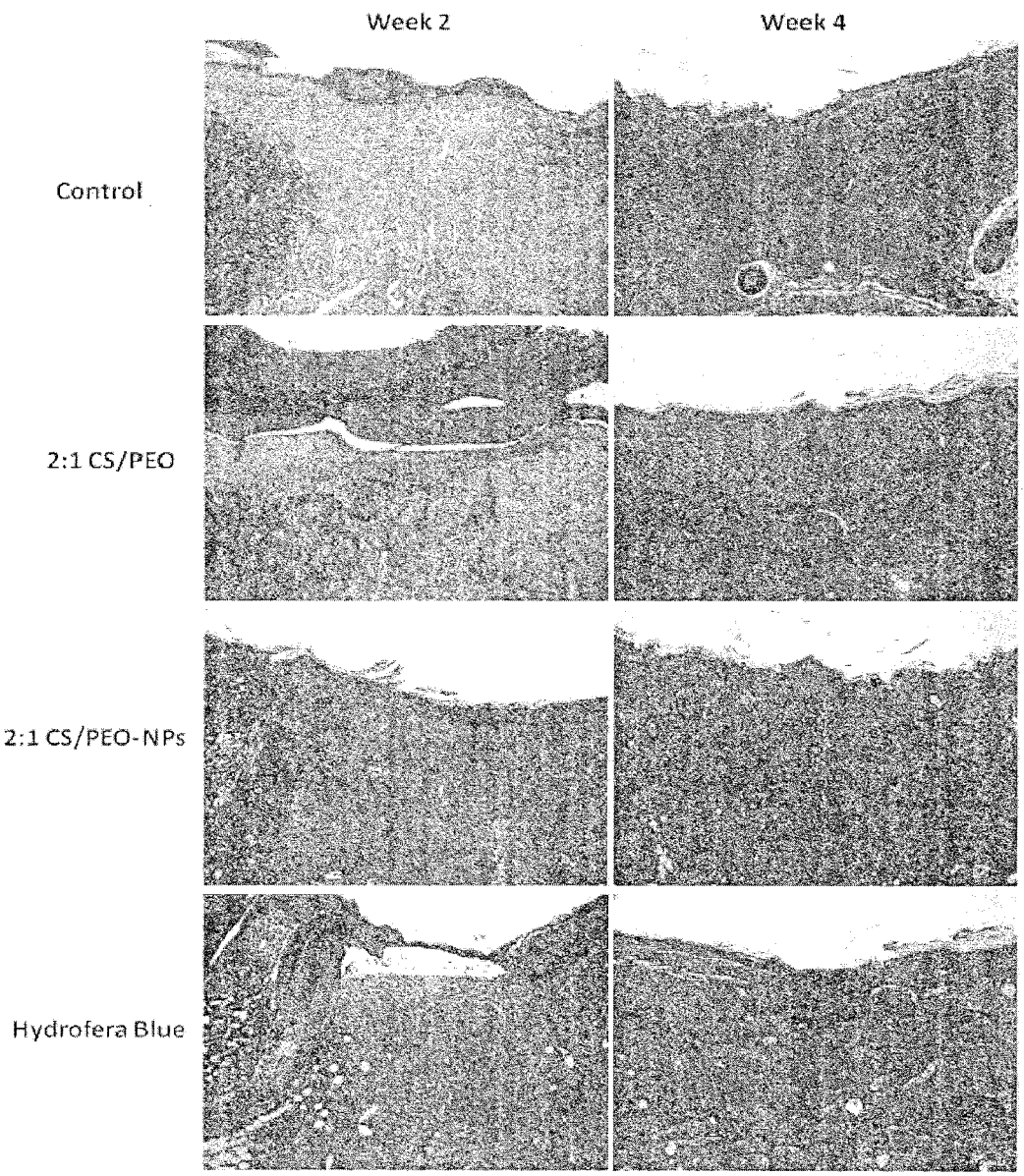
FIG. 8A illustrates staining images of wounds treated according to some embodiments of methods described herein.
Figure 8B:
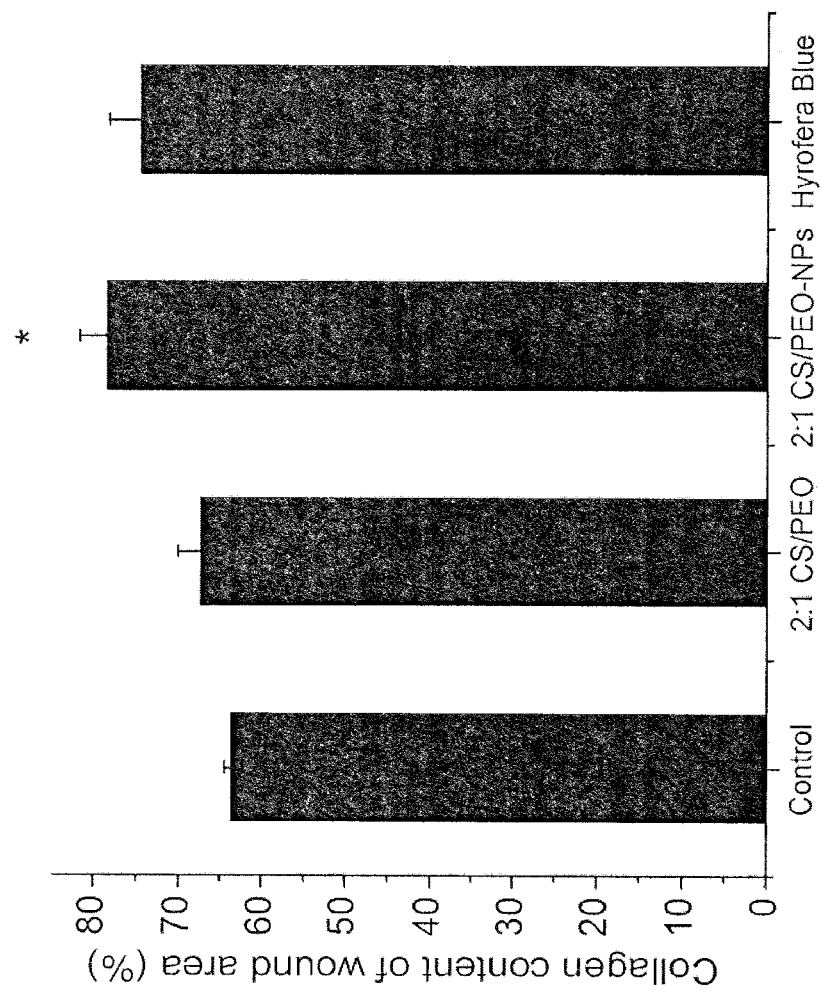
FIGS. 8B and 8C illustrate plots of the results of treating a wound according to some embodiments described of methods herein.
Figure 8C:
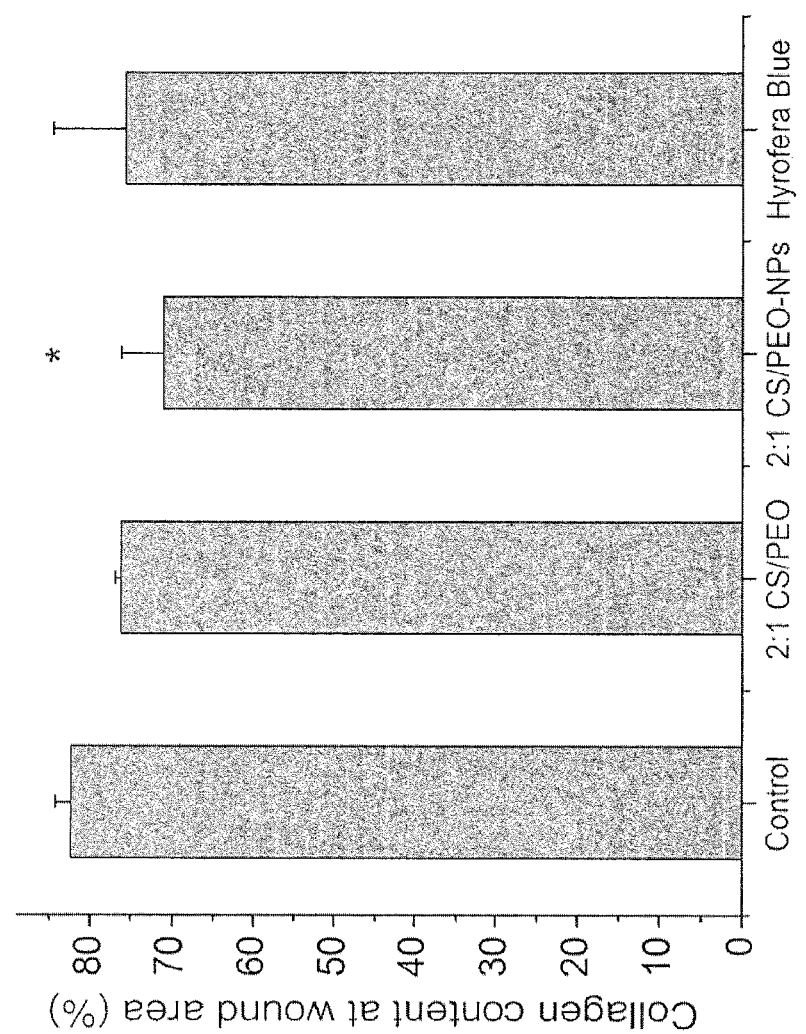

Masson's Trichrome staining was performed to assess the collagen deposition (blue) in the wound site. FIG. 8 illustrates collagen staining images and quantification of wounds treated by CS/PEO-NP meshes and Hydrofera Blue wound dressing. Specifically, FIG. 8A illustrates Masson's Trichrome staining of the control, 2:1 CS/PEO, 2:1 CS/PEO-NPs, and Hydrofera Blue samples at 2 and 4 weeks post-treatment. FIG. 8B illustrates collagen quantification of each wound area at 2 weeks, and FIG. 8C illustrates collagen quantification of each wound area at 4 weeks after treatment (*p<0.05). 2:1 CS/PEO showed a significantly (p<0.05) higher amount of collagen deposition at 2 weeks after treatment. A higher amount of myofibroblast formation at the wound site was also identified in the 2:1 CS/PEO-NPs samples compared to the open wound. Compared to open wound control and nanofibers without growth factors, more mature collagen fibers were observed for 2:1 CS/PEO-NPs samples with a lower inflammatory cell presence. More collagen tissue could help the reconstruction of ECM and further support skin tissue growth. After 4 weeks of treatment the growth factor-releasing meshes exhibited the lowest collagen content at the wound area. Not intending to be bound by theory, it is believed that this observation may be due to more mature collagen formation and increased hair follicle regeneration. Further, such morphology could indicate that a remodeling phase was already reached for 2:1 CS/PEO-NPs at 4 weeks, while other samples still remained at the tissue regeneration phase.

Example 2

Wound Dressings Comprising Stacks of Meshes

Wound dressings comprising stacks of meshes according to some embodiments described herein were prepared as follows. First, biodegradable meshes including polymers such as PLA, PLGA, PCL, collagen, hyaluronic acid (HA), gelatin, polyethylene oxide (PEO), chitosan, and carboxylmethyl chitosan (CMC) were obtained by electrospinning in a manner described hereinabove. Next, a micro-needle array with various needle sizes and densities was used to punch or perforate individual electrospun meshes to provide microholes or perforations through the individual electrospun meshes. Different sizes and densities of holes or perforations could be patterned on both hydrophobic and hydrophilic meshes. Following fabrication of individual perforated meshes, multiple meshes made of identical or different materials were stacked together to create a mesh assembly with gradually decreasing perforation sizes and/or densities from one side to the other. Such a structure allowed cells to penetrate from one side of the mesh assembly to the other side gradually. The top layer (the side opposite the wound in this Example) of each stack was formed from a non-perforated mesh. The top layer thus formed a physical barrier for tissue penetration. As described herein, such wound dressings could be used as hernia meshes for hernia repair applications.

Figure 9:
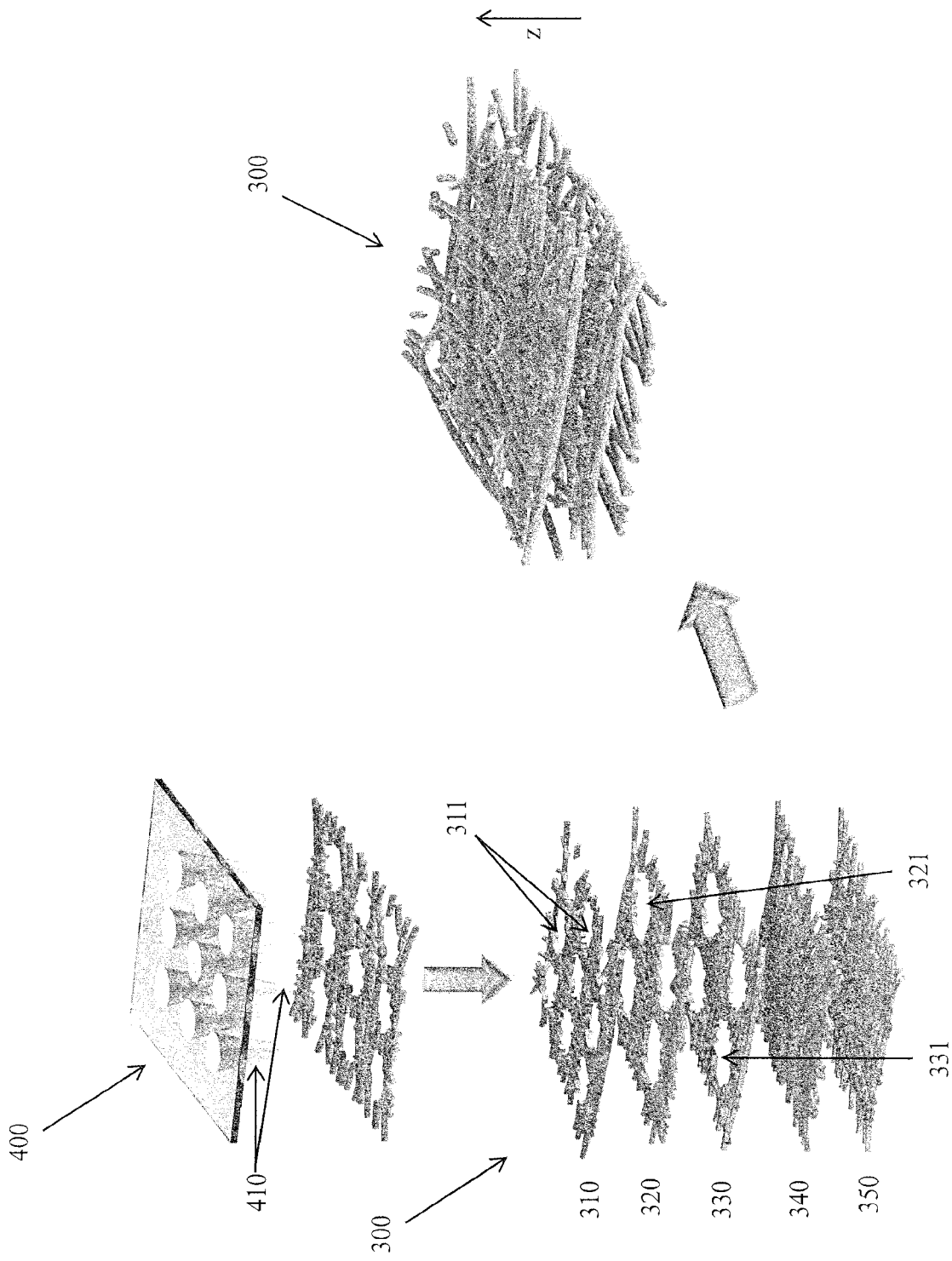
FIG. 9 illustrates schematically a method of making a wound dressing according to one embodiment described herein.
Figure 10B:
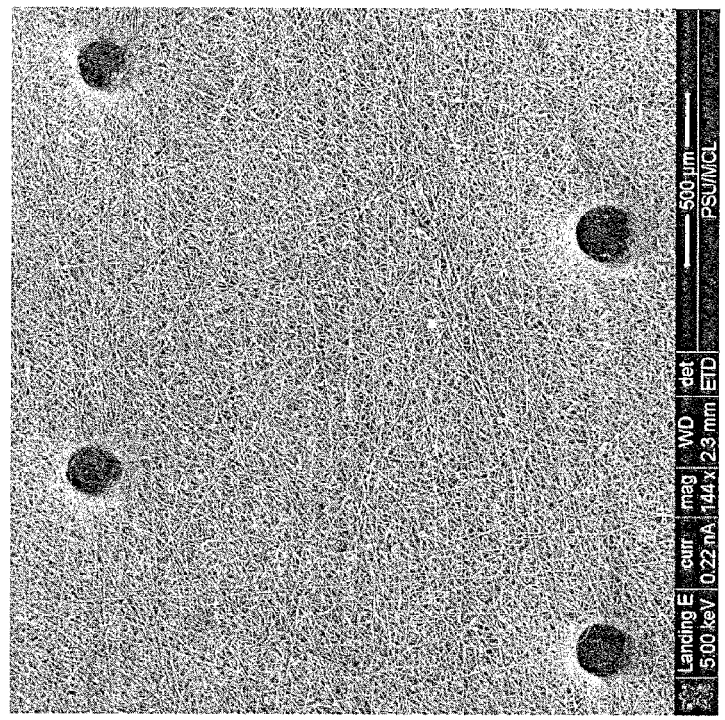
FIGS. 10A-D illustrate SEM images of perforated meshes of wound dressings according to some embodiments described herein.
Figure 10A:
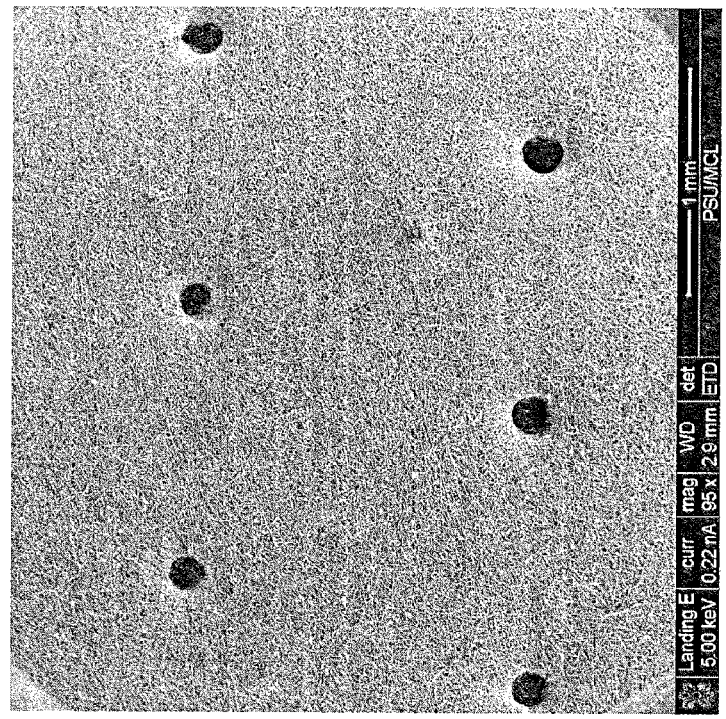
Figure 10D:
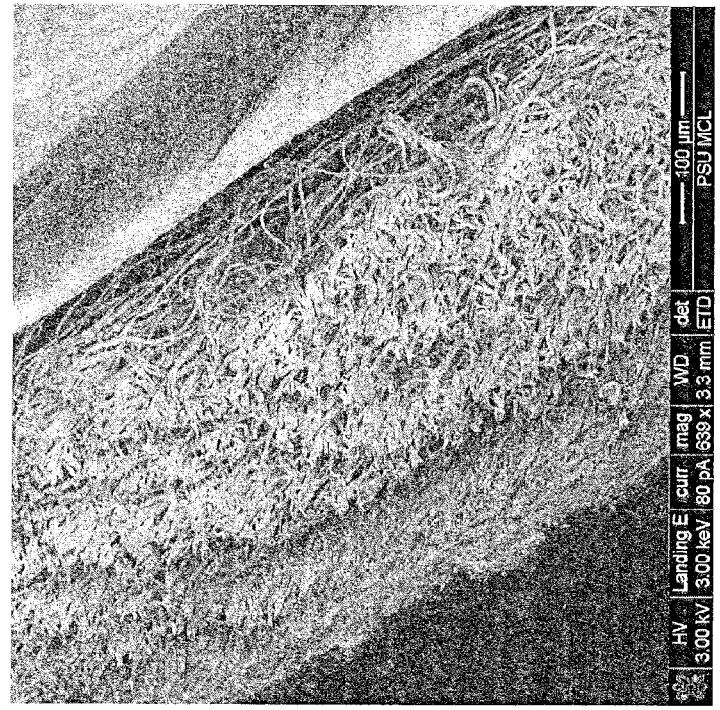
Figure 10C:
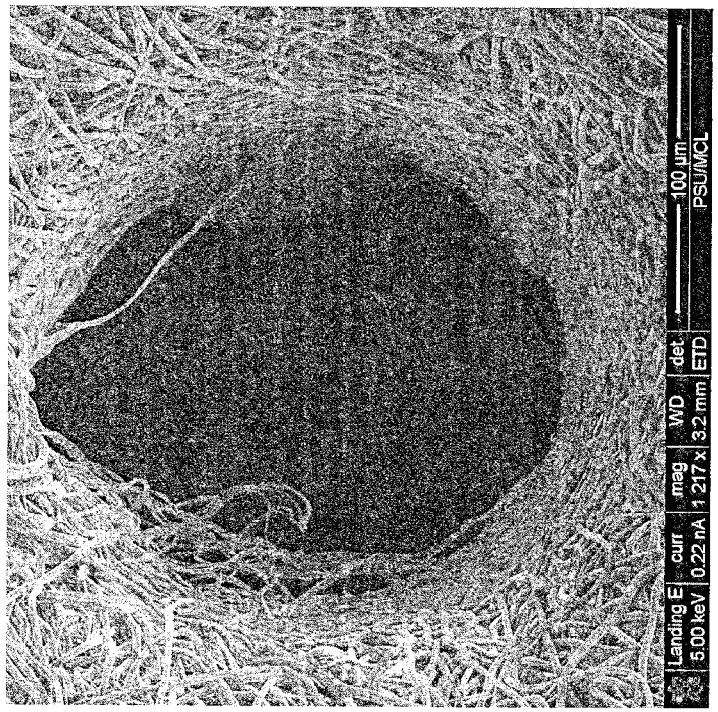

FIG. 9 illustrates the foregoing fabricating and assembling steps. Specifically, in the embodiment of FIG. 9, a stack (300) of meshes (310, 320, 330, 340, 350) is formed by electrospinning and perforating the meshes (310, 320, 330, 340, 350) individually. For perforation, a micro-patterned perforation or punch apparatus (400) is used to provide perforations or holes (311, 321, 331) in three of the meshes (310, 320, 330). The other two meshes (340, 350) are not perforated. The perforation or punch apparatus (400) comprises an array of needles (410) that can vary in needle density and/or needle size. As illustrated in FIG. 9, only the perforation of the top mesh (310) is shown. Further, in the embodiment of FIG. 9, the meshes (310, 320, 330, 340, 350) form a perforation gradient in the z-direction, where the degree of perforation decreases from the top mesh (310) toward the bottom mesh (350). In addition, in the embodiment of FIG. 9, the meshes (310, 320, 330, 340, 350) are arranged in the stack (300) in an alternating hydrophilic and hydrophobic manner. In particular, hydrophilic meshes (320, 340) alternate with hydrophobic meshes (310, 330, 350) in the stack (300).

Exemplary perforated meshes are illustrated in FIG. 10. Specifically, FIG. 10 illustrates SEM images of perforated electrospun polycaprolactone (PCL) meshes. FIGS. 10A and 10B are low magnification images. FIG. 10C is a high magnification image of a single perforation of a perforated PCL mesh. As shown in FIGS. 10A-C, the micro-needle array punched clean-cut perforations with a diameter of 150 μm and a pitch between holes of 1 mm. Such perforations could provide ample access for tissue ingrowth, unlike some other electrospun meshes whose pores are too small for cell/tissue penetration. FIG. 10D is a cross-sectional image of a 3-layer stack of meshes comprising a PCL mesh disposed in between two PEO/CMC meshes. The PEO/

CMC meshes could be easily hydrated and intimately attached to the sandwiched PCL mesh.

Figure 11B:
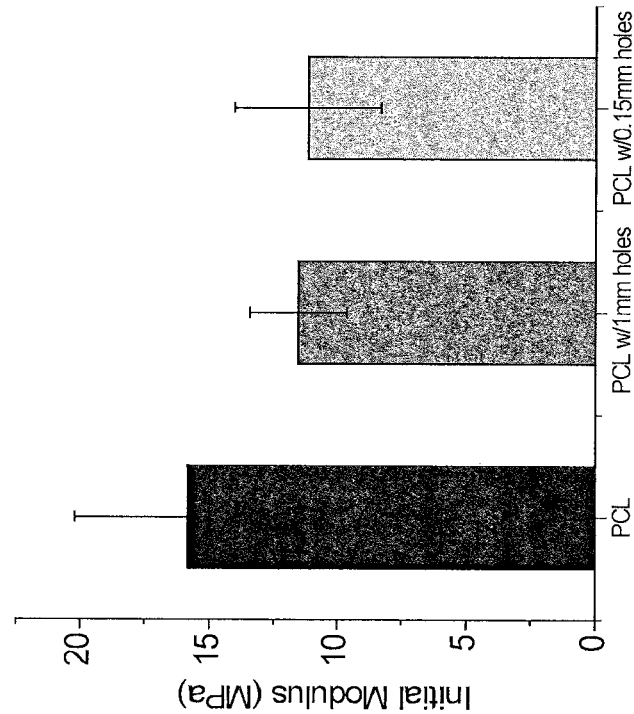
FIGS. 11A-D illustrate plots of mechanical properties of meshes of wound dressings according to some embodiments described herein.
Figure 11A:
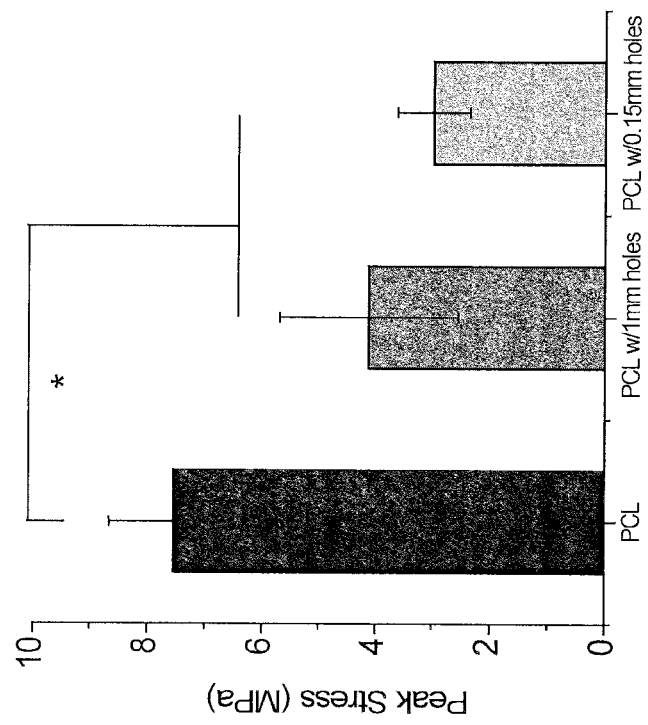
Figure 11D:
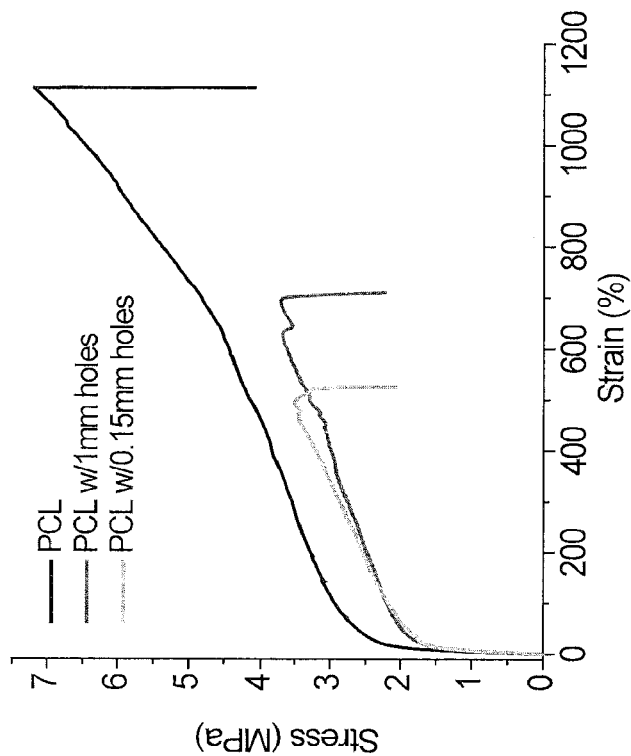
Figure 11C:
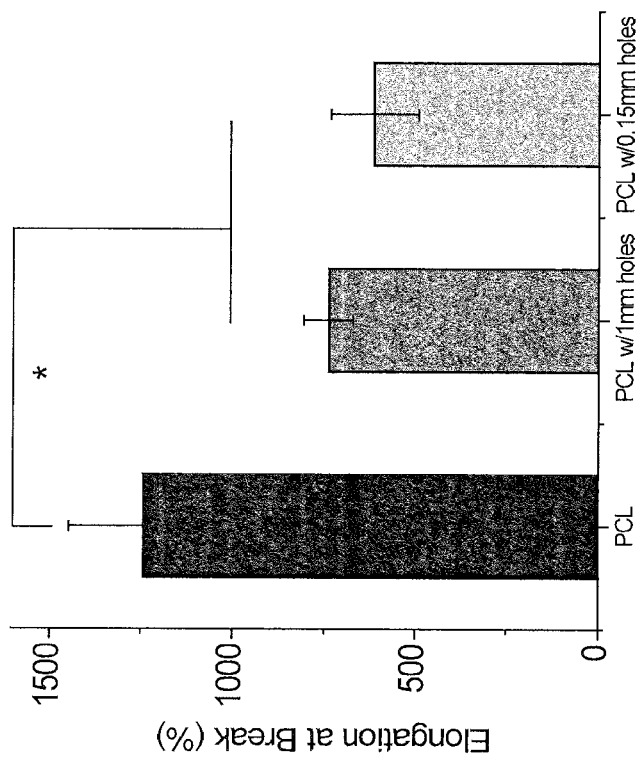

The mechanical performance of perforated and non-perforated meshes was evaluated by tensile tests. Specifically, mesh samples cut into strips with a width of 5 mm and a length of 30 mm were tested. The gauge between grips was 10 mm. The crosshead elongation speed was 100 mm/min. Some results for PCL meshes with different degrees of perforation are illustrated in FIG. 11 (*, p<0.01). Perforation densities for the meshes with 1 mm diameter perforations and 0.15 mm diameter perforations are 36 and 64 perforations/cm$^2$, respectively. FIG. 11A illustrates the peak stress of the meshes. FIG. 11B illustrates the initial (Young's) modulus of the meshes. FIG. 11C illustrates the elongation at break of the meshes. FIG. 11D illustrates a representative stress-strain curve of each sample. As illustrated in FIG. 11, The peak stress and elongation at break decreased significantly after perforation of the meshes. However, such perforated meshes were also shown to be suitable for hernia repair applications. In addition, the mechanical properties of meshes described herein, in some cases, can be tuned by varying material compositions, electrospinning conditions, and/or degree of perforation.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A wound dressing comprising:
   a plurality of meshes formed from a plurality of biodegradable polymer fibers;
   wherein the biodegradable polymer fibers comprise a first active agent;
   wherein the plurality of meshes further comprise a plurality of biodegradable polymer particles;
   wherein the biodegradable polymer particles comprise a second active agent;
   wherein an in vivo or in vitro release profile of the first active agent differs from an in vivo or in vitro release profile of the second active agent;
   wherein the plurality of meshes are arranged in a stack,
   wherein the stack has a top surface and a bottom surface, wherein the bottom surface is defined by a mesh placed on a wound and the top surface is defined by a mesh disposed farthermost from the wound, wherein the stack having a property gradient in a z-direction of the stack such that the property increases from the bottom surface to the top surface or such that the property decreases from the bottom surface to the top surface of the stack, wherein the z-direction is defined in a stacking direction; and
   wherein the plurality of meshes is at least three meshes, and wherein the property is defined by a mesh porosity or a mesh perforation.

2. The wound of claim 1, wherein the plurality of meshes comprises a first perforated mesh and a second perforated mesh arranged in the stack, the first mesh having a greater degree of perforation than the second mesh.

3. The wound dressing of claim 1, wherein the particles are disposed within the fibers of the plurality of meshes in an amount up to about 30 weight percent, based on the total weight of the fibers plus the particles.

4. The wound dressing of claim 1, wherein the in vivo or in vitro release profile of the first active agent and the in vivo or in vitro release profile of the second active agent overlap by less than about 70%.

5. The wound dressing of claim 1, wherein the biodegradable polymer fibers comprise one or more antimicrobial polymer fibers.

6. The wound dressing of claim 1, wherein the biodegradable polymer fibers comprise one or more of chitosan, carboxymethyl chitosan (CMC), and poly(ethylene oxide).

7. The wound dressing of claim 1, wherein the biodegradable polymer fibers comprise one or more polymers comprising a citrate moiety.

8. The wound dressing of claim 1, wherein the biodegradable polymer fibers comprise conductive polymer fibers comprising one or more of polypyrrole, polyaniline, or a poly-thiophene.

9. The wound dressing of claim 1, wherein the first active agent comprises a growth factor.

10. The wound dressing of claim 1, wherein the biodegradable polymer particles comprise one or more of a polyester, polylactic acid, polyglycolic acid, polylactic-co-glycolic acid, polycaprolactone, and copolymers thereof.

11. The wound dressing of claim 1, wherein the second active agent comprises a growth factor.

12. The wound dressing of claim 1, wherein the wound dressing exhibits a transfer of mechanical loads from the plurality of meshes to a regenerated biological tissue.

13. A method of treating a wound comprising: applying the wound dressing of claim 1 to a surface of the wound.

14. The method of claim 13 further comprising at least partially degrading the biodegradable polymer fibers of the wound dressing to release the first active agent into the wound.

15. The method of claim 14 further comprising at least partially degrading the biodegradable polymer particles of the wound dressing to release the second active agent into the wound, wherein the second active agent is released after the first active agent is released.

* * * * *